(12) United States Patent
Woodward et al.

(10) Patent No.: US 12,404,547 B1
(45) Date of Patent: Sep. 2, 2025

(54) METHODS AND SYSTEMS FOR MONITORING A RECIPIENT OF AN ALLOGRAFT

(71) Applicant: CareDx, Inc., Brisbane, CA (US)

(72) Inventors: Robert Woodward, Pleasanton, CA (US); Marica Grskovic, Burlingame, CA (US); James Yee, San Mateo, CA (US); Mitch Nelles, Half Moon Bay, CA (US); David Hiller, Brisbane, CA (US)

(73) Assignee: CareDx, Inc.

( * ) Notice: Subject to any disclaimer, the term of this patent is extended or adjusted under 35 U.S.C. 154(b) by 0 days.

(21) Appl. No.: 18/936,839

(22) Filed: Nov. 4, 2024

Related U.S. Application Data

(63) Continuation of application No. 18/455,456, filed on Aug. 24, 2023, now abandoned, which is a continuation-in-part of application No. 14/658,061, filed on Mar. 13, 2015, now Pat. No. 11,767,559.

(60) Provisional application No. 61/953,582, filed on Mar. 14, 2014.

(51) Int. Cl.
| | |
|---|---|
| C12P 19/34 | (2006.01) |
| C12Q 1/6806 | (2018.01) |
| C12Q 1/686 | (2018.01) |
| G16B 20/00 | (2019.01) |

(52) U.S. Cl.
CPC ........... C12Q 1/686 (2013.01); C12Q 1/6806 (2013.01); G16B 20/00 (2019.02)

(58) Field of Classification Search
CPC .................................................. C12Q 1/6869
See application file for complete search history.

(56) References Cited

U.S. PATENT DOCUMENTS

| | | | |
|---|---|---|---|
| 6,132,997 | A | 10/2000 | Shannon |
| 7,655,399 | B2 | 2/2010 | Cantor et al. |
| 9,370,689 | B2 | 6/2016 | Guillama et al. |
| 10,402,774 | B1 | 9/2019 | Phillips et al. |
| 11,479,819 | B2 | 10/2022 | Ramani |
| 2002/0197621 | A1 | 12/2002 | Drmanac |
| 2002/0197630 | A1 | 12/2002 | Knapp et al. |
| 2004/0137470 | A1 | 7/2004 | Dhallan |
| 2006/0228721 | A1 | 10/2006 | Leamon et al. |
| 2007/0095905 | A1 | 5/2007 | Kadaba |
| 2007/0248978 | A1 | 10/2007 | Lal et al. |
| 2010/0151471 | A1* | 6/2010 | Faham .................. C12Q 1/6883 435/6.16 |
| 2011/0173023 | A1 | 7/2011 | LeClair et al. |
| 2012/0295810 | A1 | 11/2012 | Quake et al. |
| 2013/0024127 | A1 | 1/2013 | Stuelpnagel et al. |
| 2013/0173028 | A1 | 7/2013 | Felty et al. |
| 2013/0178371 | A1 | 7/2013 | Oliphant et al. |
| 2014/0088995 | A1 | 3/2014 | Damani |
| 2015/0154352 | A1 | 6/2015 | Johnson et al. |
| 2015/0191787 | A1 | 7/2015 | Muthukumar et al. |
| 2015/0203916 | A1 | 7/2015 | Ikonomidis et al. |
| 2016/0115541 | A1 | 4/2016 | Schutz et al. |
| 2016/0369333 | A1 | 12/2016 | Babiarz et al. |
| 2017/0086011 | A1 | 3/2017 | Neves et al. |
| 2017/0335369 | A1 | 11/2017 | Fields et al. |
| 2018/0049675 | A1 | 2/2018 | Kerber |
| 2018/0344215 | A1 | 12/2018 | Ohnemus et al. |
| 2019/0203264 | A1* | 7/2019 | Quake .................... C12Q 1/686 |
| 2019/0213538 | A1 | 7/2019 | Bebout et al. |
| 2019/0276879 | A1 | 9/2019 | Sparks et al. |
| 2020/0048694 | A1* | 2/2020 | Godwin ................ C12Q 1/6869 |
| 2020/0226542 | A1 | 7/2020 | Lau et al. |
| 2021/0037813 | A1 | 2/2021 | Scalea et al. |
| 2021/0198733 | A1 | 7/2021 | Moshkevich et al. |
| 2021/0230697 | A1 | 7/2021 | Kurian et al. |
| 2021/0238681 | A1 | 8/2021 | Sarwal et al. |
| 2021/0301342 | A1* | 9/2021 | Lefkowitz .............. G16H 50/70 |
| 2021/0366571 | A1 | 11/2021 | Kurtz et al. |
| 2022/0051803 | A1 | 2/2022 | Nelson |
| 2022/0073989 | A1* | 3/2022 | Sarwal ................. C12Q 1/6883 |
| 2022/0093208 | A1 | 3/2022 | Lefkowitz et al. |
| 2023/0287497 | A1* | 9/2023 | Moshkevich .......... C12Q 1/686 |

(Continued)

FOREIGN PATENT DOCUMENTS

| | | |
|---|---|---|
| CN | 102618626 A | 8/2012 |
| CN | 103374518 A | 10/2013 |
| EP | 3712898 A1 | 9/2020 |

(Continued)

OTHER PUBLICATIONS

Access Array™ Barcode Library for Illumina Sequencers—384 (Bidirectional); Standard BioTools™. PN100-3771. 3 pages (2023).
Access Array System for Illumina Sequencing Systems: User guide. PN 100-3770 M1. Fluidigm Corporation. 90 pages (2019).
Agbor-Enoh Sean et al., Circulating cell-free DNA as a biomarker of tissue injury: Assessment in a cardiac xenotransplantation model. Journal of Heart and Lung Transplantation. 37(8):967-975 (2018).
Akalin Enver et al., Clinical Validation of an Immune Quiescence Gene Expression Signature in Kidney Transplantation. Kidney360. 2(12):1998-2009 (2021).
Bader, P. et al. How and when should we monitor chimerism after allogeneic stem cell transplantation?. Bone marrow transplantation 35(2):107-119 (2005).

(Continued)

*Primary Examiner* — Kenneth R Horlick
(74) *Attorney, Agent, or Firm* — Wilson Sonsini Goodrich & Rosati

(57) ABSTRACT

A method for sequencing can be used to monitor a recipient of an allograft. A sample comprising nucleic acid molecules can be provided from the recipient of the allograft. A plurality of nucleic acid molecules can be isolated from the sample and amplified. The plurality of nucleic acid molecules can be subjected to one or more amplification reactions using a plurality of primers to generate a plurality of DNA molecules. The plurality of primers can target at least 100 independent polymorphisms. The DNA molecules, or derivatives thereof, can be sequenced. The method may not require genotyping of the recipient.

22 Claims, 7 Drawing Sheets

(56) References Cited

U.S. PATENT DOCUMENTS

2023/0407392 A1    12/2023    Woodward et al.

FOREIGN PATENT DOCUMENTS

| WO | WO-2011057061 A1 | 5/2011 |
| --- | --- | --- |
| WO | WO-2012019193 A2 | 2/2012 |
| WO | WO-2012019200 A2 | 2/2012 |
| WO | WO-2013043922 A1 | 3/2013 |
| WO | WO-2013049892 A1 | 4/2013 |
| WO | WO-2013159035 A2 | 10/2013 |
| WO | WO-2014074501 A1 | 5/2014 |
| WO | WO-2014116729 A2 | 7/2014 |
| WO | WO-2014194113 A2 | 12/2014 |
| WO | WO-2015069933 A1 | 5/2015 |
| WO | WO-2018000031 A1 | 1/2018 |
| WO | WO-2020172164 A1 | 8/2020 |
| WO | WO-2021021657 A1 | 2/2021 |

OTHER PUBLICATIONS

Barker, Juliet N. et al. Transplantation of 2 partially HLA-matched umbilical cord blood units to enhance engraftment in adults with hematologic malignancy. Blood 105(3):1343-1347 (2005).

Bay, Jakob T. et al., Low C4 gene copy numbers are associated with superior graft survival in patients transplanted with a deceased donor kidney et al., , Kidney International. 84(3):562-569 (2013).

Beck, Julia et al., et al., Digital Droplet PCR for Rapid Quantification of Donor DNA in the Circulation of Transplant Recipients as a Potential Universal Biomarker of Graft Injury.Clinical Chemistry. 59(12):1732-1741 (2013).

Beszteri, . Bánk et al., Average genome size: a potential source of bias in comparative metagenomics. The ISME Journal 4(8):1075-1077 (2010).

Biswas, Chandra S. et al., Double Haploidentical Hematopoietic Stem Cell Transplantation Results in Successful Engraftment of Bone Marrow from Both Donors without Graft-versus-Host or Graft-versus-Graft Effects. Biol Blood Marrow Transplant 18:1808-1818 (2012).

Bloom, Roy D. et al. Cell-free DNA and active rejection in kidney allografts. Journal of the American Society of Nephrology 28(7):2221-2232 (2017).

Cassuto, James R. et al., Kidney transplantation in patients with a prior heart transplant et al., Transplantation 89(4): 427-433 (2010).

Cha, Rita S. and Thilly, William G. Specificity, efficiency, and fidelity of PCR. Genome Research 3(3): S18-S29. (1993).

Chiu, Rossa W. K., et al., Effects of blood-processing protocols on fetal and total DNA quantification in maternal plasma. Clinical Chemistry. 47(9):1607-1613 (2001).

Christakoudi, Sofia et al. Development of a multivariable gene-expression signature targeting T-cell-mediated rejection in peripheral blood of kidney transplant recipients validated in cross-sectional and longitudinal samples. EBioMedicine 41:571-583 (2019).

Chu, Tianjiao et al., A novel approach toward the challenge of accurately quantifying fetal DNA in maternal plasma. Prenatal Diagnosis. 30(12-13):1226-1229 (2010).

Colobran, R. et al. Copy number variation in the CCL4L gene is associated with susceptibility to acute rejection in lung transplantation. Genes & Immunity 10(3):254-259 (2009).

Crespo-Leiro, M. et al. Increased Plasma Levels of Donor-Derived Cell-Free DNA Correlate With Rejection in Heart Transplant Recipients: The Cargo II Multicenter Trial. The Journal of Heart and Lung Transplantation 34(4):S31-S32 (2015).

Davey, John W. et al. Genome-wide genetic marker discovery and genotyping using next-generation sequencing. Nature Reviews Genetics 12(7):499-510 (2011).

DbSNP—Submitted SNP(ss) details: ss1341432998, submitted Aug. 16, 2014. 2 pages (2014). Available at: https://www.ncbi.nlm.nih.gov/projects/SNP/snp_ss.cgi?subsnp_id=ss1341432998.

DbSNP Short Genetic Variations_Reference SNP(rs) Report; rs1047979. 12 pages, released Sep. 21, 2022. Retrieved from https://www.ncbi.nlm.nih.gov/snp/rs1047979.

De Vlaminck, Iwijn. et al. Circulating cell-free DNA enables noninvasive diagnosis of heart transplant rejection. Science translational medicine 6(241):241ra77, 1-8 (2014).

Dedrick, Russell L. Understanding gene expression patterns in immune-mediated disorders. Journal of Immunotoxicology 4(3):201-207 (2007).

Deng, M. C. et al. Noninvasive discrimination of rejection in cardiac allograft recipients using gene expression profiling. American Journal of Transplantation 6(1):150-160 (2006).

Deng, Yangyang. et al. Quantification of Circulating Pig-Specific DNA in the Blood of a Xenotransplantation Model. J. Vis. Exp 163:e61579, 1-12 (2020).

Dharnidharka, Vikas R, and Andrew Malone. Biomarkers to detect rejection after kidney transplantation. Pediatric Nephrology 33(7):1113-1122 (2018). Published online on Jun. 19, 2017.

Egidio, Camila et al. Universal Sensitive, Accurate and Precise Microchimerism Surveillance Solution for Allogeneic Hematopoietic Cell Transplant. Blood 136:32-33 (2020).

Feng, Kai-chao. et al. Cocktail treatment with EGFR-specific and CD133-specific chimeric antigen receptor-modified T cells in a patient with advanced cholangiocarcinoma. Journal of hematology & oncology 10:4, 1-11 (2017).

Fu, Qiang. et al. An unbiased machine learning exploration reveals gene sets predictive of allograft tolerance after kidney transplantation. Frontiers in Immunology 12:695806, 1-10 (2021).

Gadi, Vijayakrishna K. et al. Soluble donor DNA and islet injury after transplantation. Transplantation 92(5):607-611 (2011).

Gotoh, Mitsukazu. et al. Multiple donor allotransplantation: a new approach to pancreatic islet transplantation. Transplantation 45(6):1008-1011 (1988).

Gotoh, Takahiro et al., Prediction of MYCN amplification in neuroblastoma using serum DNA and real-time quantitative polymerase chain reaction. J Clin Oncology. 23(22):5205-5210 (2005).

Han, Dongmei. et al. Assessment of cytotoxic lymphocyte gene expression in the peripheral blood of human islet allograft recipients: elevation precedes clinical evidence of rejection. Diabetes 53(9):2281-2290 (2004).

Hanvesakul, Rajesh. et al. Donor HLA-C genotype has a profound impact on the clinical outcome following liver transplantation. American Journal of Transplantation 8(9):1931-1941 (2008).

Hochberg, Ephraim P. et al. A novel rapid single nucleotide polymorphism (SNP)-based method for assessment of hematopoietic chimerism after allogeneic stem cell transplantation. Blood, The Journal of the American Society of Hematology 101(1):363-369 (2003). Published online on Aug. 29, 2002.

Hollander, Zsuzsanna. et al. Whole blood biomarkers of acute cardiac allograft rejection: double-crossing the biopsy. Transplantation 90(12):1388-1393 (2010).

Hummert, C et al. Creation and comparison of different chip definition files for Affymetrix microarrays. International Conference on Bioinformatics and Computational Biology . BIOCOMP'11. pp. 16-22 (2011).

Jun, Goo. et al. Detecting and estimating contamination of human DNA samples in sequencing and array-based genotype data. The American Journal of Human Genetics 91(5):839-848 (2012).

Jun, Goo. et al. Supplemental Information: Detecting and estimating contamination of human DNA samples in sequencing and array-based genotype data. The American Journal of Human Genetics 91(5):839-848 (2012).

Kamboj, Mini. et al. The changing epidemiology of vancomycin-resistant Enterococcus (VRE) bacteremia in allogeneic hematopoietic stem cell transplant (HSCT) recipients. Biology of Blood and Marrow Transplantation 16(11):1576-1581 (2010).

Kanwar, Manreet K. et al. Impact of cytomegalovirus infection on gene expression profile in heart transplant recipients. The Journal of Heart and Lung Transplantation 40(2):101-107 (2021). Published Online on Nov. 22, 2020.

Kim, Jieun. et al. SNP-based next-generation sequencing reveals low-level mixed chimerism after allogeneic hematopoietic stem cell transplantation. Annals of Hematology 97(9):1731-1734 (2018).

(56) References Cited

OTHER PUBLICATIONS

Kurian, S. M. et al. Molecular classifiers for acute kidney transplant rejection in peripheral blood by whole genome gene expression profiling. American Journal of Transplantation 14(5):1164-1172 (2014).
Li, Hong. et al. Copy number variation in CCL3L1 gene is associated with susceptibility to acute rejection in patients after liver transplantation. Clinical transplantation 26(2):314-321 (2012).
Li, Ying. et al. Ready detection of donor-specific single-nucleotide polymorphisms in the urine of renal transplant recipients by matrix-assisted laser desorption/ionization time-of-flight mass spectrometry. Clinical chemistry 51(10):1903-1904 (2005).
Lichtenstein, Anatoly V. et al. Novel applications of polymerase chain reaction to urinary nucleic acid analysis. Clinical Applications of PCR 336:145-154 (2006).
Liu, Jun. et al. Allogeneic CD19-CAR-T cell infusion after allogeneic hematopoietic stem cell transplantation in B cell malignancies. Journal of hematology & oncology 10(1):35, 1-8 (2017).
Liu, Lin et al., Comparison of next-generation sequencing systems. Journal of Biomedicine and Biotechnology. 2012:251364, pp. 1-11 (2012).
Mao, Youying. et al. CXCL10 and CXCL13 Expression were highly up-regulated in peripheral blood mononuclear cells in acute rejection and poor response to anti-rejection therapy. Journal of clinical immunology 31(3):414-418 (2011). Published Online on Dec. 30, 2010.
Merani, Shaheed, and AM James Shapiro. Current status of pancreatic islet transplantation. Clinical science 110(6):611-625 (2006).
Miotke, Laura. et al. High sensitivity detection and quantitation of DNA copy number and single nucleotide variants with single color droplet digital PCR. Analytical chemistry 86(5):2618-2624 (2014).
Nielsen, Rasmus. et al. Genotype and SNP calling from next-generation sequencing data. Nature Reviews Genetics 12(6):443-451 (2011).
Oeth, Paul et al., Qualitative and Quantitative Genotyping Using Single Base Primer Extension Coupled with Matrix-Assisted Laser Desorption/Ionization Time-of-Flight Mass Spectrometry (MassARRAY®). Single Nucleotide Polymorphisms Methods in Molecular Biology. 578: 307-343 (2009).
Pakstis, Andrew J. et al. SNPs for a universal individual identification panel. Human genetics 127(3):315-324 (2010).
Pereira, Mariana Buongermino. et al. Comparison of normalization methods for the analysis of metagenomic gene abundance data. BMC genomics 19(1):274, 1-17 (2018).
Qiagen®: QIAamp® Circulating Nucleic Acid Handbook. 64 pages, (2019).
Quail, Michael et al., A tale of three next generation sequencing platforms: comparison of Ion Torrent, Pacific Biosciences and Illumina MiSeq sequencers. BMC Genomics. 13:341, pp. 1-13 (2012).
Samper, Isabelle C. et al. Portable microfluidic biosensing system for real-time analysis of microdialysate in transplant kidneys. Analytical chemistry 91(22):14631-14638 (2019).
Sathirapatya, Tikumphorn. et al. A SNP panel for early detection of artificial chimerism in HSCT patients using TaqMan technology. International Journal of Legal Medicine 134(5):1553-1561 (2020).
Saukkonen, Katri et al., Cell-Free Plasma DNA as a Predictor of Outcome in Severe Sepsis and Septic Shock. Clinical Chemistry 54(6):1000-1007 (2008).
Sigdel, Tara. et al. Assessment of 19 genes and validation of CRM gene panel for quantitative transcriptional analysis of molecular rejection and inflammation in archival kidney transplant biopsies. Frontiers in Medicine 6:213, 1-10 (2019).
Smith, Anajane G. et al. Comparison of sequence-specific oligonucleotide probe vs next generation sequencing for HLA-A, B, C, DRB1, DRB3/B4/B5, DQA1, DQB1, DPA1, and DPB1 typing: toward single-pass high-resolution HLA typing in support of solid organ and hematopoietic cell transplant programs. Hla 94(3):296-306 (2019).
Snyder, Thomas M. et al. Universal noninvasive detection of solid organ transplant rejection. Proceedings of the National Academy of Sciences 108(15):6229-6234 (2011).
Stein, Richard A. Next-Generation Sequencing Update. vol. 28, No. 15, 7 pages (Sep. 1, 2008). Available at https://www.genengnews.com/insights/next-generation-sequencing-update/.
Stemmer, Christine et al., Use of magnetic beads for plasma cell-free DNA extraction: toward automation of plasma DNA analysis for molecular diagnostics. Clinical Chemistry. 49(11):1953-1955 (2003).
Suzuki, Nobuyasu et al., Characterization of circulating DNA in healthy human plasma. Clinica Chimica Acta. 387(1-2):55-58 (2008).
Swinkels, Dorine W. et al., Effects of blood-processing protocols on cell-free DNA quantification in plasma. Clinical Chemistry. 49(3):525-526 (2003).
Taira, Chiaki. et al. Rapid single nucleotide polymorphism based method for hematopoietic chimerism analysis and monitoring using high-speed droplet allele-specific PCR and allele-specific quantitative PCR. Clinica Chimica Acta 445:101-106 (2015).
Tamkovich, Svetlana N. et al., Circulating nucleic acids in blood of healthy male and female donors. Clinical Chemistry. 51(7):1317-1319 (2005).
Toso, Christian. et al. Histologic graft assessment after clinical islet transplantation. Transplantation 88(11):1286-1293 (2009).
Van Loon, Elisabet. et al. Development and validation of a peripheral blood mRNA assay for the assessment of antibody-mediated kidney allograft rejection: a multicentre, prospective study. EBioMedicine 46:463-472 (2019).
Vazirabad, Ibrahim. et al. Direct HLA genetic comparisons identify highly matched unrelated donor-recipient pairs with improved transplantation outcome. Biology of Blood and Marrow Transplantation 25(5):921-931 (2019). Published online on Dec. 8, 2018.
Wagner, Ines. et al. Allele-level KIR genotyping of more than a million samples: workflow, algorithm, and observations. Frontiers in immunology 9:2843, 1-15 (2018).
Wang, H. et al. Establishment of a quantitative polymerase chain reaction assay for monitoring chimeric antigen receptor T cells in peripheral blood. Transplantation Proceedings 50(1):104-109 (2018).
Wilm, Andreas et al., LoFreq: a sequence-quality aware, ultra-sensitive variant caller for uncovering cell-population heterogeneity from high-throughput sequencing datasets. Nucleic Acids Research. 40(22):11189-11201 (2012).
Wong. L. The Evolution and Innovation of Donor-Derived Cell-Free DNA Testing in Transplantation. Journal of Medical Diagnostic Methods 9(5):302, 1-5 (2020).
Zhou, Ming. et al. Circulating pig-specific DNA as a novel biomarker for monitoring xenograft rejection. Xenotransplantation 26(4):e12522, 1-12 (2019).
Chen, Yan. et al. Peripheral blood transcriptome sequencing reveals rejection-relevant genes in long-term heart transplantation. International Journal of Cardiology 168(3):2726-2733 (2013).
Co-pending U.S. Appl. No. 18/935,347, inventors Woodward; Robert et al., filed Nov. 1, 2024.
Co-pending U.S. Appl. No. 18/935,348, inventors Woodward; Robert et al., filed Nov. 1, 2024.
Co-pending U.S. Appl. No. 18/935,360, inventors Woodward; Robert et al., filed Nov. 1, 2024.
Co-pending U.S. Appl. No. 18/936,845, inventors Woodward; Robert et al., filed Nov. 4, 2024.
European Patent Office Technical Board of Appeal decision T 1514/21 (Monitoring immunosuppressive therapies in a transplant recipient/CAREDX) Dec. 9, 2023 (Year: 2023).
Forshew, Tim. et al. Noninvasive identification and monitoring of cancer mutations by targeted deep sequencing of plasma DNA. Science Translational Medicine 4(136):136ra68, 1-12 (2012).
Forshew, Tim. et al. Supplemental Information: Noninvasive identification and monitoring of cancer mutations by targeted deep sequencing of plasma DNA. Science Translational Medicine 4(136):136ra68, 1-20 (2012).
Garcia Moreira, Vanessa. et al. Cell-free DNA as a noninvasive acute rejection marker in renal transplantation. Clinical Chemistry 55(11):1958-1966 (2009).

(56) References Cited

OTHER PUBLICATIONS

Grinyo, Josep. et al. Association of four DNA polymorphisms with acute rejection after kidney transplantation. Transplant International 21(9):879-891 (2008).
Invivioscribe, Instructions for Use Amplification Control. General Purpose Reagent :1-13 (2020).
Ro, Han et al. Association of polymorphisms of interleukin-8, CXCR1, CXCR2, and selectin with allograft outcomes in kidney transplantation. Transplantation 91(1):57-64 (2011).
Scherer, Andreas. Clinical and ethical considerations of massively parallel sequencing in transplantation science. World Journal of Transplantation 3(4):62-67 (2013).
Sigdel, Tara K. et al. A rapid noninvasive assay for the detection of renal transplant injury. Transplantation 96(1):97-101 (2013).
Technology Spotlight: Illumina Sequencing Technology. Illumina :1-4 (2009).
Using a PhiX Control for HiSeq Sequencing Runs. Illumina Technical Note: Sequencing :1-2 (2013).
Yu, Stephanie CY. et al. High-resolution profiling of fetal DNA clearance from maternal plasma by massively parallel sequencing. Clinical Chemistry 59(8):1228-1237 (2013).
Zhong, Xiao Yan. et al. Cell-free DNA in urine: a marker for kidney graft rejection, but not for prenaStal diagnosis?. Annals of the New York Academy of Sciences 945(1):250-257 (2001).
Jiang, Peiyong, et al. FetalQuant: deducing fractional fetal DNA concentration from massively parallel sequencing of DNA in maternal plasma. Bioinformatics, 2012, vol. 28, No. 22, pp. 2883-2890.
Qiagen, QIAquick PCR Purification Kit Protocol, Jul. 2008, p. 19-20 (2008).

* cited by examiner dd-cfDNA $P=0.017$
AUC = 0.68 (95% CI 0.56-0.80)

AlloMap $P=0.007$
AUC = 0.68 (95% CI 0.56-0.80)

Combined $P<0.0001$
AUC = 0.78 (95% CI 0.67-0.87)

METHODS AND SYSTEMS FOR MONITORING A RECIPIENT OF AN ALLOGRAFT

CROSS-REFERENCE TO RELATED APPLICATIONS

This application is a continuation of U.S. application Ser. No. 18/455,456, filed Aug. 24, 2023, which is a continuation-in-part of U.S. application Ser. No. 14/658,061, filed Mar. 13, 2015, now issued as U.S. Pat. No. 11,767,559 on Sep. 26, 2023, which claims the benefit of U.S. Provisional Application No. 61/953,582, filed Mar. 14, 2014, all of which are hereby incorporated by reference in their entirety.

FIELD

The present disclosure relates to methods and systems for isolating nucleic acids for sequencing.

BACKGROUND

The immune system plays a defensive role in subjects, such as a human individual, but can also cause diseases, disorders, and other undesirable conditions. In the case of medically intended transplantation of non-self (allograft) cells, tissues, or organs into an individual, the recipient's immune system recognizes the allograft to be foreign to the body and activates various mechanisms to reject the allograft. Thus, it is necessary to medically suppress the normal immune system responses to reject the transplant. The medical practice of immunosuppression in transplant recipients has evolved to include a regimen of prophylactic pharmacologic agents, typically beginning with induction therapies to deplete lymphocytes, followed by maintenance drugs intended to inhibit activation or replication of lymphocytes such as corticosteroids, calcineurin inhibitors (such as tacrolimus), and additional inhibitors of lymphocyte replication (such as mycophenolate mofetil). Changing or varying the amount of immunosuppressive drugs administered to a transplant recipient has largely been guided by empirical experience. After transplant, the dosage of immunosuppressant(s) are reduced over time to reduce the incidence and severity of side effects, such as increased risk of infectious diseases, while still avoiding immune rejection of the allograft.

After transplantation, the status of the allograft in the transplant recipient may be monitored for the remainder of his/her lifetime, including assessment function of the allograft and immune-mediated rejection of the allograft. In heart transplantation, for example, surveillance for rejection may include up to 15 scheduled biopsies within the first year of the transplant to provide specimens of the heart muscle for histologic evaluation by a pathologist. Each biopsy procedure is invasive (percutaneous passage of a transvenous catheter into the right ventricle of the heart), stressful, inconvenient, and incumbent of procedural risks for the patient, as well as being expensive. Moreover, the biopsy sampling is extremely localized, so histological abnormalities in any non-biopsied areas of the heart are missed. The grading of biopsies is subjective, and discordance of biopsy findings is common between independent pathologists. In the standard clinical care of transplant recipients, there are a variety of clinical laboratory diagnostics tests, in addition to periodic biopsies, that provide some information relating to the status of the allograft. For example, the serum trough levels of the calcineurin inhibitor drug are measured to estimate adequacy of intended coverage. Other assays detect the presence of antibodies directed against the allograft. Biopsy is primarily used for surveillance of transplant rejection within the first year, but this invasive method is not well suited or established for guiding individualized immunosuppressive therapy in the longer term (e.g beyond one year after transplant) maintenance care of patients. Noninvasive gene expression methods inform on the status of the immune system by examining the status of genes expressed in immune cells. AlloMap Molecular Expression Testing is an FDA-cleared test available for heart transplant recipients. Tests are in development for monitoring other solid organ transplants.

In addition to existing invasive biopsy methods of monitoring transplant status, there are currently no specific tests with a demonstrated ability to guide individualization (and further minimization) of immunosuppressive drugs for long-term maintenance of a transplant recipient. Data, mostly derived from registry studies, have identified certain clinical risk factors for transplant loss or death such as recipient age, gender, and race, as well as donor features such as cold ischemia, time, and age. However, determining these clinical risk factors does not supplant the need for individualized treatment and routine surveillance of transplant recipients.

There exists a need for improved noninvasive methods of diagnosing and monitoring that status of an allograft in a transplant recipient, as well as for methods of determining the need to adjust immunosuppressive therapy being administered to a transplant recipient.

BRIEF SUMMARY

In one aspect, the present disclosure relates to methods of monitoring immunosuppressive therapy in a subject, the method including: a) providing cell-free DNA from a sample obtained from a subject who is the recipient of an organ transplant from a donor, b) sequencing a panel of single nucleotide polymorphisms (SNPs) from the cell-free DNA, where the panel of SNPs is suitable for differentiating between donor-derived cell-free DNA and recipient-derived cell-free DNA, c) assaying variance in SNP allele distribution patterns in the panel as compared to expected homozygous or heterozygous distribution patterns to determine the level of donor-derived cell-free DNA, and d) diagnosing the status of the transplanted organ in the subject, where a change in levels or variance of the donor-derived cell-free DNA over a time interval is indicative of transplanted organ status and a basis for adjusting immunosuppressive therapy.

In another aspect, the present disclosure relates to methods of adjusting an immunosuppressive therapy in a subject, the method including: a) providing cell-free DNA from a sample obtained from a subject who is the recipient of an organ transplant from a donor, b) sequencing a panel of single nucleotide polymorphisms (SNPs) from the cell-free DNA, where the panel of SNPs is suitable for differentiating between donor-derived cell-free DNA and recipient-derived cell-free DNA, c) assaying variance in SNP allele distribution patterns in the panel as compared to expected homozygous or heterozygous distribution patterns to determine the level of donor-derived cell-free DNA, d) diagnosing the status of the transplanted organ in the subject, where a change in levels or variance of the donor-derived cell-free DNA over a time interval is indicative of transplanted organ status, e) adjusting immunosuppressive therapy being administered to the subject.

In some embodiments that may be combined with any of the preceding embodiments, an increase in the levels or variance of the donor-derived cell-free DNA over the time interval is indicative of transplant rejection, a need for adjusting immunosuppressive therapy, and/or a need for further investigation of the transplanted organ status. In some embodiments that may be combined with any of the preceding embodiments, a decrease in the levels or variance of the donor-derived cell-free DNA over the time interval is indicative of transplant tolerance, a need for adjusting immunosuppressive therapy, and/or a need for further investigation of the transplanted organ status. In some embodiments that may be combined with any of the preceding embodiments, no change in the levels or variance of the donor-derived cell-free DNA over the time interval is indicative of stable transplant rejection status and/or opportunity for adjusting immunosuppressive therapy. In some embodiments that may be combined with any of the preceding embodiments, immunosuppressive therapy being administered to the subject is increased. In some embodiments that may be combined with any of the preceding embodiments, immunosuppressive therapy being administered to the subject is decreased. In some embodiments that may be combined with any of the preceding embodiments, immunosuppressive therapy being administered to the subject is maintained. In some embodiments that may be combined with any of the preceding embodiments, the organ transplant is a kidney transplant. In some embodiments that may be combined with any of the preceding embodiments, the organ transplant is a heart transplant. In some embodiments that may be combined with any of the preceding embodiments, the sample is a plasma sample. In some embodiments that may be combined with any of the preceding embodiments, the panel of SNPs includes at least 20 independent SNPs. In some embodiments that may be combined with any of the preceding embodiments, the panel of SNPs includes independent SNPs selected from rs1004357, rs10092491, rs1019029, rs1027895, rs10488710, rs10500617, rs1058083, rs10768550, rs10773760, rs10776839, rs1109037, rs12480506, rs1294331, rs12997453, rs13134862, rs13182883, rs13218440, rs1336071, rs1358856, rs1410059, rs1478829, rs1490413, rs1498553, rs1523537, rs1554472, rs159606, rs1736442, rs1821380, rs1872575, rs2046361, rs2073383, rs214955, rs2175957, rs221956, rs2255301, rs2269355, rs2270529, rs2272998, rs2291395, rs2292972, rs2342747, rs2399332, rs2503107, rs2567608, rs279844, rs2811231, rs2833736, rs2920816, rs315791, rs321198, rs338882, rs3744163, rs3780962, rs4288409, rs430046, rs4364205, rs445251, rs4530059, rs4606077, rs464663, rs4789798, rs4796362, rs4847034, rs521861, rs560681, rs5746846, rs576261, rs590162, rs6444724, rs6591147, rs6811238, rs689512, rs6955448, rs7041158, rs7205345, rs722290, rs7229946, rs740598, rs7520386, rs7704770, rs8070085, rs8078417, rs891700, rs901398, rs9546538, rs9606186, rs985492, rs9866013, rs987640, rs9905977, rs993934, and rs9951171. In some embodiments that may be combined with any of the preceding embodiments, sequencing the panel of SNPs is performed using a multiplex sequencing platform. In some embodiments that may be combined with any of the preceding embodiments, the time interval is about 12-14 months after the transplant from the donor to the recipient subject occurred. In some embodiments that may be combined with any of the preceding embodiments, the method further includes testing for viral load. In some embodiments, the testing includes determining the presence of a virus selected from CMV, EBV, anellovirus, and BKV. In some embodiments that may be combined with any of the preceding embodiments, the method further includes conducting one or more gene expression profiling assays. In some embodiments, the gene expression profiling assay is an AlloMap test.

In one aspect, the present disclosure relates to methods of monitoring the status of a transplanted organ in a subject, the method including: a) providing cell-free DNA from a sample obtained from a subject who is the recipient of an organ transplant from a donor, b) sequencing a panel of single nucleotide polymorphisms (SNPs) from the cell-free DNA, where the panel of SNPs is suitable for differentiating between donor-derived cell-free DNA and recipient-derived cell-free DNA, c) assaying variance in SNP allele distribution patterns in the panel as compared to expected homozygous or heterozygous distribution patterns to determine the level of donor-derived cell-free DNA, and d) diagnosing the status of the transplanted organ in the subject, where a change in levels or variance of the donor-derived cell-free DNA over a time interval is indicative of the status of the transplanted organ.

In another aspect, the present disclosure relates to methods of monitoring immunosuppressive therapy in a subject, the method including: a) providing cell-free DNA from a sample obtained from a subject who is the recipient of an organ transplant from a donor, b) sequencing a panel of single nucleotide polymorphisms (SNPs) from the cell-free DNA, where the panel of SNPs is suitable for differentiating between donor-derived cell-free DNA and recipient-derived cell-free DNA, c) assaying variance in SNP allele distribution patterns in the panel as compared to expected homozygous or heterozygous distribution patterns to determine the level of donor-derived cell-free DNA, and d) diagnosing the status of the transplanted organ in the subject, where a change in levels or variance of the donor-derived cell-free DNA over a time interval is indicative of transplanted organ status and a basis for adjusting immunosuppressive therapy.

In another aspect, the present disclosure relates to methods of adjusting an immunosuppressive therapy in a subject, the method including: a) providing cell-free DNA from a sample obtained from a subject who is the recipient of an organ transplant from a donor, b) sequencing a panel of single nucleotide polymorphisms (SNPs) from the cell-free DNA, where the panel of SNPs is suitable for differentiating between donor-derived cell-free DNA and recipient-derived cell-free DNA, c) assaying variance in SNP allele distribution patterns in the panel as compared to expected homozygous or heterozygous distribution patterns to determine the level of donor-derived cell-free DNA, d) diagnosing the status of the transplanted organ in the subject, where a change in levels or variance of the donor-derived cell-free DNA over a time interval is indicative of transplanted organ status, and e) adjusting immunosuppressive therapy being administered to the subject.

In some embodiments that may be combined with any of the preceding embodiments, an increase in the levels or variance of the donor-derived cell-free DNA over the time interval is indicative of transplant rejection, a need for adjusting immunosuppressive therapy, and/or a need for further investigation of the transplanted organ status. In some embodiments that may be combined with any of the preceding embodiments, a decrease in the levels or variance of the donor-derived cell-free DNA over the time interval is indicative of transplant tolerance, a need for adjusting immunosuppressive therapy, and/or a need for further investigation of the transplanted organ status. In some embodiments that may be combined with any of the preceding embodiments, no change in the levels or variance of the donor-derived cell-free DNA over the time interval is indicative of stable transplant rejection status and/or opportunity for adjusting immunosuppressive therapy. In some embodiments that may be combined with any of the preceding embodiments, immunosuppressive therapy being administered to the subject is increased. In some embodiments that may be combined with any of the preceding embodiments, immunosuppressive therapy being administered to the subject is decreased. In some embodiments that may be combined with any of the preceding embodiments, immunosuppressive therapy being administered to the subject is maintained. In some embodiments that may be combined with any of the preceding embodiments, the organ transplant is a kidney transplant. In some embodiments that may be combined with any of the preceding embodiments, the organ transplant is a heart transplant. In some embodiments that may be combined with any of the preceding embodiments, the organ transplant is selected from a liver transplant, a lung transplant, and a pancreas transplant. In some embodiments that may be combined with any of the preceding embodiments, the sample is a plasma sample. In some embodiments that may be combined with any of the preceding embodiments, the panel of SNPs includes independent SNPs selected from rs1004357, rs10092491, rs1019029, rs1027895, rs10488710, rs10500617, rs1058083, rs10768550, rs10773760, rs10776839, rs1109037, rs12480506, rs1294331, rs12997453, rs13134862, rs13182883, rs13218440, rs1336071, rs1358856, rs1410059, rs1478829, rs1490413, rs1498553, rs1523537, rs1554472, rs159606, rs1736442, rs1821380, rs1872575, rs2046361, rs2073383, rs214955, rs2175957, rs221956, rs2255301, rs2269355, rs2270529, rs2272998, rs2291395, rs2292972, rs2342747, rs2399332, rs2503107, rs2567608, rs279844, rs2811231, rs2833736, rs2920816, rs315791, rs321198, rs338882, rs3744163, rs3780962, rs4288409, rs430046, rs4364205, rs445251, rs4530059, rs4606077, rs464663, rs4789798, rs4796362, rs4847034, rs521861, rs560681, rs5746846, rs576261, rs590162, rs6444724, rs6591147, rs6811238, rs689512, rs6955448, rs7041158, rs7205345, rs722290, rs7229946, rs740598, rs7520386, rs7704770, rs8070085, rs8078417, rs891700, rs901398, rs9546538, rs9606186, rs985492, rs9866013, rs987640, rs9905977, rs993934, and rs9951171. In some embodiments that may be combined with any of the preceding embodiments, the panel of SNPs includes SNPs that have an overall population minor allele frequency of >0.4, a target population minor allele frequency of >0.4, the lowest polymerase error rate of the 6 potential allele transitions or transversions, and the genomic distance between each independent SNP is >500 kb. In some embodiments that may be combined with any of the preceding embodiments, the panel of SNPs includes independent SNPs selected from rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. In some embodiments, the SNP panel includes about 195 to about 200, about 200 to about 205, about 210 to about 215, about 215 to about 220, about 220 to about 225, about 225 to about 230, about 230 to about 235, about 235 to about 240, about 240 to about 245, about 245 to about 250, about 250 to about 255, about 255 to about 260, about 260 to about 265, or about 260 to about 266 of the independent SNPs. In some embodiments that may be combined with any of the preceding embodiments, the SNP panel includes rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. In some embodiments that may be combined with any of the preceding embodiments, sequencing the panel of SNPs is performed using a multiplex sequencing platform. In some embodiments that may be combined with any of the preceding embodiments, the level of donor-derived cell-free DNA in the sample is determined without using genotype information. In some embodiments that may be combined with any of the preceding embodiments, the method further includes testing for the presence of an infectious agent. In some embodiments that may be combined with any of the preceding embodiments, the infectious agent is selected from viruses, bacteria, fungi, and parasites. In some embodiments, the viruses are selected from Cytomegalovirus, Epstein-Barr virus, Anelloviridae, and BK virus. In some embodiments that may be combined with any of the preceding embodiments, the method further includes conducting one or more gene expression profiling assays. In some embodiments, a combination score is calculated based on the results of the level of donor-derived cell-free DNA and the results of the gene expression profiling assay. In some embodiments that may be combined with any of the preceding embodiments, the gene expression profiling assay is an AlloMap test.

DESCRIPTION OF THE FIGURES

FIG. 6A illustrates dd-cfDNA levels from heart transplant recipients. cfDNA data was generated using plasma from heart transplant recipients collected in PPT tubes. Patient samples were assigned R (rejection) status based on the status of endomyocardial biopsy performed at the same patient visit. Donor-derived cell-free DNA is expressed as a percent of the total cell-free DNA, measured as described herein. FIG. 6B illustrates AlloMap data from the transplant recipients in FIG. 6A. Gene expression data was generated using mononuclear cells collected using CPT tubes. Gene expression was measured by AlloMap Molecular Expression Testing. FIG. 6C illustrates combined dd-cfDNA data and AlloMap data. The values for dd-cfDNA (FIG. 6A) and AlloMap (FIG. 6B) were scaled to the same range and additively combined. The combined score is better at discriminating rejection from non-rejection than either cfDNA or gene expression alone, as measured by the area under the curve of a receiver-operator characteristics plot.

DETAILED DESCRIPTION

Figure 1:
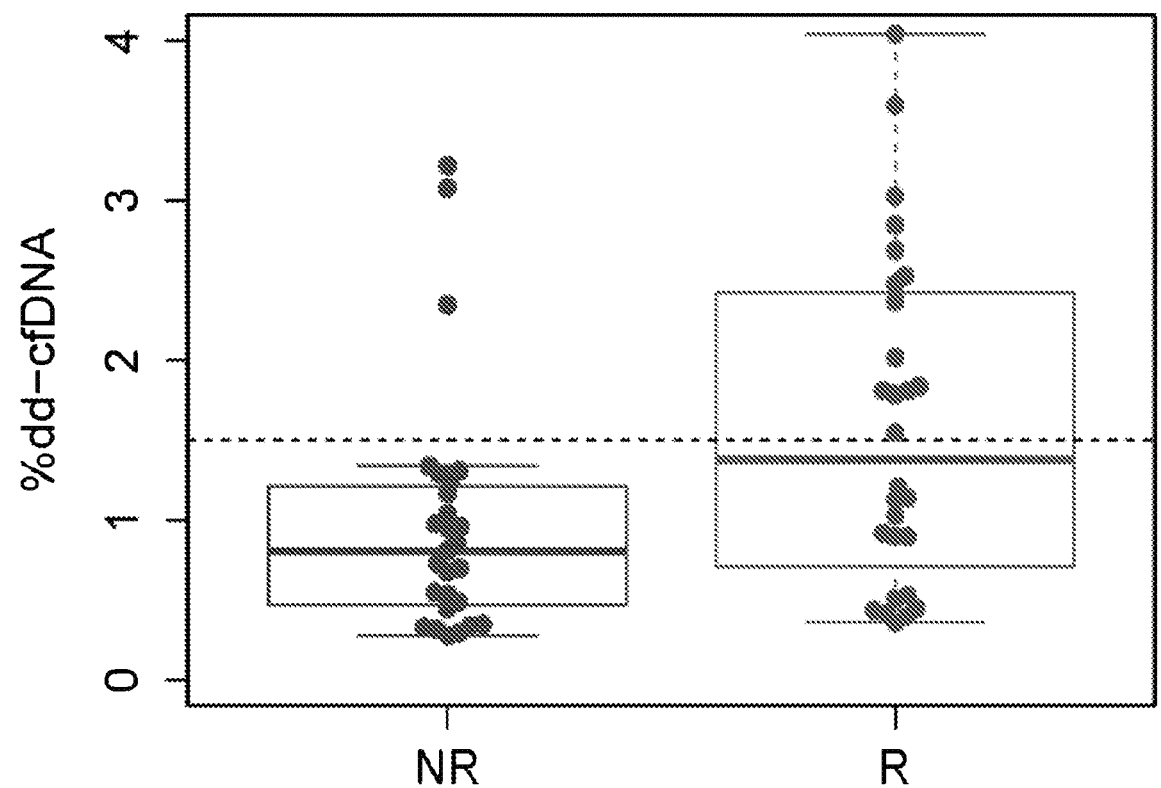
FIG. 1 illustrates that donor-derived cell-free DNA (dd-cfDNA) is greater in plasma taken from heart transplant recipients experiencing acute cellular rejection than from those not experiencing rejection. Data was generated using plasma from heart transplant recipients collected in PPT tubes. Patient samples were assigned to NR (non-rejection) and R (rejection) categories based on the status of endomyocardial biopsy performed at the same patient visit. Donor-derived cell-free DNA is expressed as a percent of the total cell-free DNA, measured as described herein. Groups differ by t-test (P=0.017).

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to methods of monitoring the status of an allograft in a transplant recipient, as well as to methods of monitoring and adjusting immunosuppressive therapies being administered to the transplant recipient.

Overview

The present disclosure is based, at least in part, on Applicant's development of techniques for probing the status of an allograft in a transplant recipient. Transplant recipients contain an allograft that is foreign to the recipient's body. This triggers an immune response from the recipient's immune system, which may lead to acute and/or chronic transplant rejection. Applicant's methods involve the analysis of cell-free DNA (cfDNA) from the transplant recipient to diagnose the status of the transplant and inform the need to adjust immunosuppressive therapy being administered to the transplant recipient. Without wishing to be bound by theory, it is thought that transplant rejection is associated with the death of cells in the transplanted (donor) organ or tissue, which will release donor-derived DNA from the dying donor cells, thus releasing donor-derived cell-free DNA (dd-cfDNA) into the bloodstream of the recipient. To assay the status of the allograft in the recipient, cell-free DNA can be extracted from a sample from the recipient, such as a bodily fluid, and various polymorphic markers, such as single nucleotide polymorphism (SNP) loci, can be sequenced, where the panel of polymorphic markers, such as a panel of SNPs, is suitable for differentiating between donor-derived cell-free DNA and recipient-derived cell-free DNA (rd-cfDNA). The specific polymorphic markers selected to be on the panel include those that are identified as having low probabilities of being identical in any two individuals, thus making them appropriate for differentiating between recipient-derived cell free DNA and donor-derived cell-free DNA. The number of polymorphic markers on the panel such as, for example, the number of SNPs on the panel, will be sufficient to discriminate between recipient and donor alleles even in related individuals (excepting identical twins). The allele distribution patterns of polymorphic markers in the panel can be assayed to determine variance in the patterns as compared to expected homozygous (i.e. 0% or 100% of each allele) or heterozygous (i.e. 50% of each allele) distribution patterns, which can be used to determine the level of donor-derived cell-free DNA. Individual genotyping of the donor and the recipient to determine which allele of the polymorphic locus belongs to the donor and/or the recipient is not necessary, as variance in the polymorphic marker allele distribution pattern from expected homozygous or heterozygous distribution patterns informs the presence of donor-derived cell-free DNA in the population of cell-free DNA molecules isolated from the transplant recipient. In other words, it is assumed that the majority signal from the cell-free DNA sample is recipient-derived DNA and that the minority signal is donor-derived DNA, and this information can be used to calculate the levels of donor-derived DNA in the cell-free DNA sample. Changes in the levels or variance of the donor-derived cell-free DNA over time can be used to inform the status of the allograft in the transplant recipient, as well as inform a need to adjust or maintain an immunosuppressive therapy being administered to the subject.

Accordingly, the present disclosure provides methods of monitoring the status of an allograft in a transplant recipient, as well as methods of monitoring and/or adjusting an immunosuppressive therapy being or to be administered to a transplant recipient. Monitoring the status of an allograft involves analyzing various aspects which provide useful information about the physiological state of the allograft such as, for example, the level of donor-derived cell-free DNA in a sample from the transplant recipient. The methods of the present disclosure may be used to predict the risk of future transplant rejection such as, for example, the risk of rejection within the following 3-6 months after analysis of samples from the transplant recipient. The methods of the present disclosure may also be used to diagnose or predict the risk of allograft dysfunction, such as chronic renal insufficiency or cardiac allograft vasculopathy (CAV) (e.g. within the next 1-2 years after analysis of samples from the transplant recipient). The methods of the present disclosure may also be used provide an assessment of the immune status of the transplant recipient, which may be used to guide decisions regarding immunosuppressive therapy in the transplant recipient. The methods of the present disclosure may also be used to guide decisions related to adjustment of immunosuppressive therapies being administered to the transplant recipient. Additional benefits and/or uses of the methods of the present disclosure will be readily apparent to one of skill in the art.

Cell-Free DNA

The methods of the present disclosure involve the analysis of cell-free DNA from a transplant recipient to diagnose the status of the transplant and/or to inform a need to adjust immunosuppressive therapy being administered to the transplant recipient. Cell-free DNA generally refers to DNA that is present outside of a cell such as, for example, DNA that is present in a bodily fluid (e.g. blood, plasma, serum, etc.) of a subject. Cell-free DNA may have originated from various locations within a cell. Cell-free DNA may have originated from, for example, nuclear DNA and mitochondrial DNA. Without wishing to be bound by theory, it is believed that cell-free DNA is released from cells via apoptosis or necrosis of the cells (i.e. cell death). Accordingly, and without wishing to be bound by theory, it is believed that during transplant rejection, apoptosis or necrosis of transplanted (donor) cells will result in donor-derived cell-free DNA being released into the bodily fluid of a transplant recipient. Transplant recipients undergoing transplant rejection may then have a cell-free DNA population in their bodily fluids which includes both their own endogenous cell-free DNA (recipient-derived cell-free DNA) as well as cell-free DNA that originated from the donor (donor-derived cell-free DNA). Determining a change in the levels and/or variance in donor-derived cell-free DNA in a transplant recipient over time according to the methods of the present disclosure may be used to diagnose the status of the allograft and inform a need to adjust immunosuppressive therapy.

Cell-free RNA may also be collected from a transplant recipient and analyzed by analogous methods as described above and also analysis of recipient RNA levels from specific marker genes to diagnose the status of the transplant and/or to inform a need to adjust immunosuppressive therapy being administered to the transplant recipient. Thus, the methods of the present disclosure generally relate to analysis of cell-free nucleic acids from a transplant recipient to diagnose the status of the transplant and/or to inform a need to adjust immunosuppressive therapy being administered to the transplant recipient.

Subjects and Samples

The methods of the present disclosure involve providing cell-free DNA from a sample obtained from a subject who is the recipient of an allograft from a donor. In this sense, the subject is a transplant recipient who contains an allograft from a donor, and is typically a human transplant recipient. The transplant recipient may have received one or more of a variety of allografts from a donor. Allografts may include transplanted organs. Transplanted organs may include, for example, a heart, a kidney, a lung, a liver, a pancreas, a cornea, an organ system, or other solid organs. The transplant received by the transplant recipient from the donor may also include other allografts such as, for example, a bone marrow transplant, pancreatic islet cells, stem cells, skin tissue, skin cells, or a xenotransplant.

The provided sample may include a bodily fluid isolated from the transplant recipient. Samples obtained from the transplant recipient contain cell-free DNA, and the total cell-free DNA present in the sample may be entirely recipient-derived cell-free DNA, or the total cell-free DNA present in the sample may include a mixture of recipient-derived cell-free DNA and donor-derived cell-free DNA. Samples may include a bodily fluid from the transplant recipient such as, for example, plasma, serum, whole blood, sweat, tears, saliva, ear flow fluid, sputum, fluid from bone marrow suspension, lymph fluid, urine, saliva, semen, vaginal flow, cerebrospinal fluid, brain fluid, ascites, milk, secretions of the respiratory, and intestinal or genitourinary tract fluids. In some embodiments where the sample is plasma, plasma derived from the venous blood of the transplant recipient can be obtained.

Once a sample is obtained, it can be used directly, frozen, or otherwise stored in a condition that maintains the integrity of the cell-free DNA for short periods of time by preventing degradation and/or contamination with genomic DNA or other nucleic acids. The amount of a sample that is taken at a particular time may vary, and may depend on additional factors, such as any need to repeat analysis of the sample. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

Samples may be taken from a transplant recipient over a period of time (i.e. over a time interval). The time at which samples are taken from the transplant recipient following the transplant event may vary. Samples may be taken from a transplant recipient at various times and over various periods of time for use in determining the status of the allograft according to the methods of the present disclosure. For example, samples may be taken from the transplant recipient within days and weeks after, about three months after, about six months after, about nine months after, or less than one year after the transplant event. Samples may be taken from the transplant recipient at various times before the one year anniversary of the transplant event, at the one year anniversary of the transplant event, or at various times after the one year anniversary of the transplant event. For example, at the one year anniversary after a transplant, samples may begin to be taken from the transplant recipient at month 12 (i.e. the one year anniversary of the transplant event) and continue to be taken for periods of time after this. In some embodiments, the time period for obtaining samples from a transplant recipient is within the first few days after the transplant from the donor to the recipient occurred. This may be done to monitor induction therapy. In some embodiments, the time period for obtaining samples from a transplant recipient is during tapering of the immunosuppressive regimen, a period that occurs during the first 12 months after the transplant from the donor to the recipient occurred. In some embodiments, the time period for obtaining samples from a transplant recipient is during the initial long term immunosuppressive maintenance phase, beginning about 12-14 months after the transplant from the donor to the recipient occurred. In some embodiments, the time period for obtaining samples from a transplant recipient is during the entire long term maintenance of the immunosuppressive regimen, any time beyond 12 months after the transplant from the donor to the recipient occurred.

Where multiple samples are to be obtained from a transplant recipient, the frequency of sampling may vary. After samples have begun to be taken from a transplant recipient, samples may be obtained about once every week, about once every 2 weeks, about once every 3 weeks, about once every month, about once every two months, about once every three months, about once every four months, about once every five months, about once every six months, about once every year, or about once every two years or more after the initial sampling event.

In some embodiments, a transplant recipient has samples of bodily fluid taken for one to three consecutive months, starting at the one year anniversary of the transplant event (i.e. 12 months after the transplant event), providing a total of 4-6 samples for analysis taken over a three month time period, with samples being collected about every two weeks. In some embodiments, a transplant recipient has samples of bodily fluid taken once a week for one to three consecutive months, starting at the one year anniversary of the transplant event (i.e. 12 months after the transplant event), providing a total of twelve samples for analysis taken over a three month time period. The total duration of obtaining samples from a transplant recipient, as well as the frequency of obtaining such samples, may vary and will depend on a variety of factors, such as clinical progress. For example, a transplant recipient may have samples obtained for analysis of cell-free DNA for the duration of their lifetime. Appropriate timing and frequency of sampling will be able to be determined by one of skill in the art for a given transplant recipient.

Analysis of Cell-Free DNA in a Transplant Recipient

The methods of the present disclosure involve the analysis of cell-free DNA from a transplant recipient. After cell-free DNA has been isolated from a transplant recipient, various methods and techniques may be used to analyze the cell-free DNA. Analysis of cell-free DNA according to the methods of the present disclosure involves analysis of a panel of polymorphic markers from the cell-free DNA. In some embodiments, the polymorphic markers are single nucleotide polymorphisms (SNPs). In some embodiments, SNPs are selected to be included in the panel at least in part on the basis that the panel of SNPs will be sufficient to differentiate between donor-derived cell-free DNA and recipient-derived cell-free DNA.

Panels of Polymorphic Markers

Analysis of cell-free DNA obtained from a transplant recipient involves the analysis of a panel of polymorphic markers from the cell-free DNA. Various polymorphic markers may be selected for inclusion in the panel to be analyzed as long as the polymorphic marker panel as a whole is suitable for differentiating between donor-derived cell-free DNA and recipient-derived cell-free DNA. The same polymorphic marker panel may be used for each transplant recipient; there is no need to customize polymorphic marker panels to individualize the panel to different transplant recipients.

Various types of polymorphic markers may be included in polymorphic marker panels. Polymorphic markers are found at a region of DNA containing a polymorphism. A polymorphism generally refers to the occurrence of two or more genetically determined alternative sequences or alleles in a population. A polymorphic marker or site is the locus at which divergence, or the polymorphism, occurs. A polymorphism may contain, for example, one or more base changes, an insertion, a repeat, or a deletion. A polymorphic locus may be as small as one base pair, such as a SNP. Polymorphic markers may include, for example, single nucleotide polymorphisms (SNPs), restriction fragment length polymorphisms (RFLPs), short tandem repeats (STRs), variable number of tandem repeats (VNTRs), hypervariable regions, minisatellites, dinucleotide repeats, trinucleotide repeats, tetranucleotide repeats, simple sequence repeats, and insertion elements. Polymorphic markers may contain one or more bases modified by methylation. Additional types of polymorphisms and polymorphic markers will be readily apparent to one of skill in the art. A polymorphism between two nucleic acids can be naturally occurring, or may be caused by exposure to or contact with chemicals, enzymes, or other agents, or exposure to agents that cause damage to nucleic acids such as, for example, ultraviolet radiation, mutagens, or carcinogens.

Various combinations of polymorphic marker types may be used in polymorphic marker panels. For example, the polymorphic marker panel may include both SNPs and short tandem repeats, or any other type of polymorphic marker. In some embodiments, the polymorphic marker panel is composed entirely of SNPs; thus, the polymorphic marker panel is a SNP panel. Additional combinations of polymorphic markers on polymorphic marker panels will be readily apparent to one of skill in the art.

Selection of the appropriate quantity and identity of polymorphic markers to be analyzed from cell-free DNA may vary, as will be appreciated by one of skill in the art. The panel of polymorphic markers to be analyzed may include at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115, at least 120, at least 150, at least 200, at least 250, at least 300, at least 350, at least 400, at least 450, at least 500, at least 1,000, or at least 1,500 or more independent polymorphic markers.

In some embodiments, the polymorphic marker panel is a panel of SNPs. SNPs to be included in the SNP panel, or in any other polymorphic marker panel, may be those previously identified as being suitable for differentiating between any two unrelated individuals (Pakstis et al., 2010). For example, the SNP panel may include one or more of the following human SNPs (named according to dbSNP numbering): rs1004357, rs10092491, rs1019029, rs1027895, rs10488710, rs10500617, rs1058083, rs10768550, rs10773760, rs10776839, rs1109037, rs12480506, rs1294331, rs12997453, rs13134862, rs13182883, rs13218440, rs1336071, rs1358856, rs1410059, rs1478829, rs1490413, rs1498553, rs1523537, rs1554472, rs159606, rs1736442, rs1821380, rs1872575, rs2046361, rs2073383, rs214955, rs2175957, rs221956, rs2255301, rs2269355, rs2270529, rs2272998, rs2291395, rs2292972, rs2342747, rs2399332, rs2503107, rs2567608, rs279844, rs2811231, rs2833736, rs2920816, rs315791, rs321198, rs338882, rs3744163, rs3780962, rs4288409, rs430046, rs4364205, rs445251, rs4530059, rs4606077, rs464663, rs4789798, rs4796362, rs4847034, rs521861, rs560681, rs5746846, rs576261, rs590162, rs6444724, rs6591147, rs6811238, rs689512, rs6955448, rs7041158, rs7205345, rs722290, rs7229946, rs740598, rs7520386, rs7704770, rs8070085, rs8078417, rs891700, rs901398, rs9546538, rs9606186, rs985492, rs9866013, rs987640, rs9905977, rs993934, and rs9951171.

SNPs may also be selected on the basis that they have, for example, an overall population minor allele frequency of >0.4, a target population minor allele frequency of >0.4, the lowest polymerase error rate (in the test system) of the 6 potential allele transitions or transversions, and low linkage on the genome such as, for example, >500 kb distance between SNPs.

The SNP panel may include, for example, one or more of the following human SNPs (named according to dbSNP numbering): rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. In some embodiments, each of the 266 above mentioned SNPs is included in the polymorphic marker panel to be analyzed from cell-free DNA.

The SNP panel may include, for example, at least at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115, at least 120, at least 150, at least 200, at least 205, at least 210, at least 215, at least 220, at least 225, at least 230, at least 235, at least 240, at least 245, at least 250, at least 255, at least 260, or at least 265 of the 266 independent SNPs identified above.

The SNP panel may include, for example, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, about 190 to about 200, about 200 to about 210, about 210 to about 220, about 220 to about 230, about 230 to about 240, about 240 to about 250, about 250 to about 260, or about 250 to about 266 of the 266 independent SNPs identified above.

The SNP panel may include, for example, about 195 to about 200, about 200 to about 205, about 210 to about 215, about 215 to about 220, about 220 to about 225, about 225 to about 230, about 230 to about 235, about 235 to about 240, about 240 to about 245, about 245 to about 250, about 250 to about 255, about 255 to about 260, about 260 to about 265, or about 260 to about 266 of the 266 independent SNPs identified above.

Amplification and Sequencing

Cell-free DNA isolated from a transplant recipient may be amplified for downstream techniques and analysis, such as analysis of a panel of polymorphic markers from the cell-free DNA. Various methods and protocols for DNA extraction are well-known in the art and are described herein (See e.g. Current Protocols in Molecular Biology, latest edition). Cell-free DNA may be extracted using the QIAamp circulating nucleic acid kit or other appropriate commercially available kits. Other exemplary methods of extracting cell-free DNA are well-known (See, e.g., Cell-Free Plasma DNA as a Predictor of Outcome in Severe Sepsis and Septic Shock. Clin. Chem. 2008, v. 54, p. 1000-1007; Prediction of MYCN Amplification in Neuroblastoma Using Serum DNA and Real-Time Quantitative Polymerase Chain Reaction. JCO 2005, v. 23, p. 5205-5210; Circulating Nucleic Acids in Blood of Healthy Male and Female Donors. Clin. Chem. 2005, v. 51, p. 1317-1319; Use of Magnetic Beads for Plasma Cell-free DNA Extraction: Toward Automation of Plasma DNA Analysis for Molecular Diagnostics. Clin. Chem. 2003, v. 49, p. 1953-1955; Chiu RWK, Poon LLM, Lau TK, Leung TN, Wong EMC, Lo YMD. Effects of blood-processing protocols on fetal and total DNA quantification in maternal plasma. Clin Chem 2001; 47:1607-1613; and Swinkels et al. Effects of Blood-Processing Protocols on Cell-free DNA Quantification in Plasma. Clinical Chemistry, 2003, vol. 49, no. 3, 525-526).

Methods of amplifying DNA are similarly well-known in the art and are described herein. Amplification generally refers to any device, method or technique that can generate copies of a nucleic acid. Amplification of cell-free DNA may involve, for example, polymerase chain reaction (PCR) techniques such as linear amplification (cf. U.S. Pat. No. 6,132,997), rolling circle amplification, and the like. Cell-free DNA may be amplified for use in downstream analysis of the DNA by, for example, digital PCR or sequencing. The Fluidigm Access Array™ System, the RainDance Technologies RainDrop system, or other technologies for multiplex amplification may be used for multiplex or highly parallel simplex DNA amplification. Amplification may involve the use of high-fidelity polymerases such as, for example, FastStart High Fidelity (Roche), Expand High Fidelity (Roche), Phusion Flash II (ThermoFisher Scientific), Phusion Hot Start II (ThermoFisher Scientific), KAPA HiFi (Kapa BioSystems), or KAPA2G (Kapa Biosystems).

Amplification may include an initial PCR cycle that adds a unique sequence to each individual molecule, called molecular indexing. Molecular indexing allows for quantitative assessment of the absolute level of both alleles for each SNP amplicon and therefore may improve precision and accuracy of determining the percent donor-derived cell-free DNA.

Amplified DNA may also be subjected to additional processes, such as indexing (also referred to as barcoding or tagging). Methods of indexing DNA are well-known in the art and are described herein. Indexing will allow for the use of multiplex-sequencing platforms, which are compatible with a variety of sequencing systems, such as Illumina HiSeq, MiSeq, and ThermoFisher Scientific Ion PGM and Ion Proton. In some embodiments, the methods provided herein include isolating the cell-free DNA in a partition (e.g., a droplet) and conducting one or more tagging reactions. Multiplex sequencing permits the sequencing of DNA from multiple samples at once through the use of DNA indexing to specifically identify the sample source of the sequenced DNA.

The amount of DNA that is used for analysis may vary. In some embodiments, less than 1 pg, 5 pg, 10 pg, 20 pg, 30 pg, 40 pg, 50 pg, 100 pg, 200 pg, 500 pg, 1 ng, 5 ng, 10 ng, 20 ng, 30 ng, 40 ng, 50 ng, 100 ng, 200 ng, 500 ng, 1 µg, 5 µg, 10 µg, 20 µg, 30 µg, 40 µg, 50 µg, 100 µg, 200 µg, 500 µg or 1 mg of DNA are obtained from the sample for further genetic analysis. In some cases, about 1-5 pg, 5-10 pg, 10-100 pg, 100 pg-1 ng, 1-5 ng, 5-10 ng, 10-100 ng, or 100 ng-1 µg of DNA are obtained from the sample for further genetic analysis.

The methods of the present disclosure involve sequencing target loci from cell-free DNA, as well as analyzing sequence data. Various methods and protocols for DNA sequencing and analysis are well-known in the art and are described herein. For example, DNA sequencing may be accomplished using high-throughput DNA sequencing techniques. Examples of next generation and high-throughput sequencing include, for example, massively parallel signature sequencing, polony sequencing, 454 pyrosequencing, Illumina (Solexa) sequencing with HiSeq, MiSeq, and other platforms, SOLID sequencing, ion semiconductor sequencing (Ion Torrent), DNA nanoball sequencing, heliscope single molecule sequencing, single molecule real time (SMRT) sequencing, MassARRAY®, and Digital Analysis of Selected Regions (DANSR™). See, e.g., Stein RA (1 Sep. 2008). "Next-Generation Sequencing Update". Genetic Engineering & Biotechnology News 28 (15); Quail, Michael; Smith, Miriam E; Coupland, Paul; Otto, Thomas D; Harris, Simon R; Connor, Thomas R; Bertoni, Anna; Swerdlow, Harold P; Gu, Yong (1 Jan. 2012). "A tale of three next generation sequencing platforms: comparison of Ion torrent, pacific biosciences and illumina MiSeq sequencers". BMC Genomics 13 (1): 341; Liu, Lin; Li, Yinhu; Li, Siliang; Hu, Ni; He, Yimin; Pong, Ray; Lin, Danni; Lu, Lihua; Law, Maggie (1 Jan. 2012). "Comparison of Next-Generation Sequencing Systems". Journal of Biomedicine and Biotechnology 2012:1-11; Qualitative and quantitative genotyping using single base primer extension coupled with matrix-assisted laser desorption/ionization time-of-flight mass spectrometry (MassARRAY®). Methods Mol Biol. 2009; 578: 307-43; Chu T, Bunce K, Hogge WA, Peters DG. A novel approach toward the challenge of accurately quantifying fetal DNA in maternal plasma. Prenat Diagn 2010; 30:1226-9; and Suzuki N, Kamataki A, Yamaki J, Homma Y. Characterization of circulating DNA in healthy human plasma. Clinica chimica acta; international journal of clinical chemistry 2008; 387:55-8). Similarly, software programs for primary and secondary analysis of sequence data are well-known in the art.

Where there are multiple cell-free DNA samples from a transplant recipient to be sequenced, such as when multiple samples are taken from the transplant recipient over time, each sample may be sequenced individually, or multiple samples may be sequenced together using multiplex sequencing.

Analyzing Polymorphic Marker Allele Distribution Patterns and Determining the Level of Donor-Derived Cell-Free DNA The methods of the present disclosure involve assaying variance in polymorphic marker allele distribution patterns in a polymorphic marker panel as compared to expected homozygous or heterozygous distribution patterns. Analysis of these patterns allows for the determination of the level of donor-derived cell-free DNA in a cell-free DNA sample obtained from a transplant recipient.

Generally, an individual contains DNA that is either homozygous or heterozygous for a given polymorphic marker, such as a SNP. An individual may be homozygous for one allele of a given polymorphic marker and will contain 100% of one allele of that polymorphic marker and will contain 0% of the other allele of that polymorphic marker (e.g. 100% of allele A for given polymorphic marker, 0% of allele B for given polymorphic marker). An individual may also be heterozygous for a given polymorphic marker, and thus will contain 50% of allele A and 50% of allele B of that polymorphic marker. Accordingly, if all of the DNA in a sample originated from a single individual, it is expected that any given polymorphic marker in the DNA in that sample will exhibit a homozygous distribution pattern (i.e. 100% of one allele, 0% of the other allele) or a heterozygous distribution pattern (i.e. 50% of one allele and 50% of the other allele). However, if a DNA sample contains DNA that originated from more than one individual (e.g. a cell-free DNA sample from a transplant recipient that contains both recipient-derived DNA and donor-derived DNA), then polymorphic marker allele distributions may vary, for a given polymorphic marker, from expected homozygous or heterozygous distribution patterns. This is so because two individuals may not necessarily share the same zygosity for a given polymorphic marker (e.g. individual 1 is homozygous for a given allele of a given polymorphic marker, and individual 2 is heterozygous for the alleles of that same polymorphic marker). When this occurs, variance in the expected allele distribution patterns as compared to expected homozygous or heterozygous distribution patterns may be observed. This variance can be used to assess whether foreign DNA is present in a DNA sample from a single individual. With respect to the methods of the present disclosure, variance in polymorphic marker allele distribution patterns in the polymorphic marker panel as compared to expected homozygous or heterozygous distribution patterns is used to determine the level of donor-derived cell-free DNA in the cell-free DNA sample obtained from a transplant recipient.

When analyzing polymorphic marker sequence data from cell-free DNA according to methods of the present disclosure, a majority signal from an allele of a polymorphic marker may be observed and a minority signal from an allele of a polymorphic marker may be observed. Regarding cell-free DNA isolated from a transplant recipient, as it is assumed that the majority of the DNA in the cell-free DNA sample from the transplant recipient originated from the recipient's own endogenous DNA, it is further assumed that the majority signal represents an allele of a polymorphic marker that originated from recipient-derived cell-free DNA, while the minority signal represents an allele of a polymorphic marker that originated from donor-derived cell-free DNA. Polymorphic markers such as SNPs, for example, with an even distribution of both alleles are assumed to have largely both originated from the recipient. Deviations from the even distribution will indicate the influence of alleles from the donor-derived cell-free DNA.

Various calculations may be performed based on allele calls from the sequence data. For example, the methods of the present disclosure may involve calculating various cell-free DNA concentrations, or percents thereof, of a total amount of cell-free DNA. Overall, as it is assumed that the majority signal from cell-free DNA in a sample isolated from a transplant recipient is recipient-derived DNA and that the minority signal is donor-derived DNA, this information can be used to calculate a percentage of donor-derived DNA in the cell-free DNA sample.

As described above, individual genotyping of the donor and the recipient to determine which allele of the polymorphic marker belongs to the donor and/or the recipient is not necessary, as variance in the polymorphic marker allele distribution pattern from expected homozygous or heterozygous distribution patterns informs the presence of donor-derived cell-free DNA in the population of cell-free DNA molecules isolated from the transplant recipient. Accordingly, the level of donor-derived cell-free DNA in a sample obtained from a transplant recipient may be determined without using genotype information from the transplant recipient, from the transplant donor, and/or any other genotype information from any source. Such genotype information that need not be considered includes, for example, the genotype across the genome as a whole or portions thereof, or the genotype at the particular polymorphic markers being analyzed. In some embodiments, individual genotyping of the transplant recipient is not performed. In some embodiments, individual genotyping of the transplant donor is not performed. In some embodiments, neither the transplant recipient nor the transplant donor are individually genotyped. In some embodiments, genotype information from the transplant recipient is not considered when determining the levels of donor-derived cell-free DNA in a sample obtained from a transplant recipient. In some embodiments, genotype information from the transplant donor is not considered when determining the levels of donor-derived cell-free DNA in a sample obtained from a transplant recipient. In some embodiments, the levels of donor-derived cell-free DNA in a sample obtained from a transplant recipient are determined without consideration of genotype information from the transplant recipient and without consideration of genotype information of the transplant donor. In some embodiments, the level of donor-derived cell-free DNA in a sample obtained from a transplant recipient may be determined without using genotype information.

Improvements to the calculations may include estimating and subtracting a level of signal due to amplification or sequencing error to improve accuracy and precision. For example, a suitably chosen subset of SNPs may be used to estimate a sum, mean, median or standard deviation of the subset to produce a computation of the overall level of donor-derived cell-free DNA. Multiple samples from the same subject at a given time of sampling will all have the same pattern of polymorphic distributions across the SNPs, which can be used to enhance the estimate of donor-derived cell-free DNA in individual samples from that subject.

The quantity of donor-derived cell-free DNA present in the cell-free DNA sample may be expressed in a variety of ways. In some embodiments, the amount of one or more DNA molecules from donor-derived cell-free DNA is determined as a percentage of the total the DNA molecules in the sample. In some embodiments, the amount of one or more DNA molecules from donor-derived cell-free DNA is determined as a ratio of the total DNA in the sample. In some embodiments, the amount of one or more DNA molecules from donor-derived cell-free DNA is determined as a ratio or percentage compared to one or more reference DNA molecules in the sample. For example, the total amount of donor-derived cell-free DNA can be determined to be 10% of the total DNA molecules in the cell-free DNA sample. Alternatively, the total amount of donor-derived cell-free DNA can be at a ratio of 1:10 compared to the total DNA molecules in the cell-free DNA sample. In some embodiments, the amount of one or more DNA molecules from the donor-derived cell-free DNA can be determined as a concentration. For example, the total amount of donor-derived cell-free DNA in the cell-free DNA sample can be determined to be 1 µg/mL. The values described here are merely exemplary to illustrate various ways to express quantities of donor-derived cell-free DNA. The percentage of donor-derived cell-free DNA in the cell-free DNA sample from a transplant recipient may be extremely low (e.g. at or below 0.5% of the total DNA content of the cell-free DNA sample). It is noted that the quantity of recipient-derived cell-free DNA in the cell-free DNA sample may also be expressed in the manners as described for donor-derived cell-free DNA. Additional methods of expressing the quantity of a given source, type, or sequence of DNA molecule in a cell-free DNA sample will be readily apparent to one of skill in the art.

The above-described embodiments of the present disclosure may be implemented in a variety of ways. For example, some aspects of the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general-purpose hardware (e.g., one or more processors) that is programmed using microcode or software to perform the functions recited above.

In this respect, it should be noted that implementation of various features of the present disclosure may use at least one non-transitory computer-readable storage medium (e.g., a computer memory, a floppy disk, a compact disk, a tape, etc.) encoded with a computer program (i.e., a plurality of instructions), which, when executed on a processor, performs the above-discussed functions. The computer-readable storage medium can be transportable such that the program stored thereon can be loaded onto any computer resource to implement certain aspects of the present disclosure discussed herein. In addition, it should be noted that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement certain aspects of the present disclosure.

Determining Status of an Allograft

The methods of the present disclosure for determining the levels of donor-derived cell-free DNA in a sample from a transplant recipient can be used to determine the status of the allograft in the transplant recipient. In general, changes in the levels or variance of donor-derived cell-free DNA beyond a suitable threshold value in the transplant recipient over time are informative with regard to the status of the allograft.

A threshold or threshold value generally refers to any predetermined level or range of levels that is indicative of the presence or absence of a condition or the presence or absence of a risk. The threshold value can take a variety of forms. It can be single cut-off value, such as a median or mean. As another example, a threshold value can be determined from baseline values before the presence of a condition or risk or after a course of treatment. Such a baseline can be indicative of a normal or other state in the subject not correlated with the risk or condition that is being tested for. For example, the baseline value may be the level of donor-derived cell-free DNA in samples from a transplant recipient prior to the actual transplant event, which would be presumably zero or negligible, but may also indicate baseline error in the system. In some embodiments, the threshold value can be a baseline value of the subject being tested. The threshold value, as it pertains to demarcating significant changes in the levels or variance of donor-derived cell-free DNA in a transplant recipient, may vary considerably. One of skill in the art would recognize appropriate parameters and means for determining significant changes in the levels or variance of donor-derived cell-free DNA in a transplant recipient over time. Once appropriate analysis parameters are selected, determining changes in the level or variance of donor-derived cell-free DNA in the transplant recipient over a period of time can inform status of the allograft.

In some embodiments, an increase in the levels or variance of the donor-derived cell-free DNA in the transplant recipient over time is indicative of transplant rejection, a need for adjusting immunosuppressive therapy, immunosuppressive treatment nephrotoxicity, infection, and/or a need for further investigation of the allograft status. Without wishing to be bound by theory, it is believed that if the level of donor-derived cell-free DNA is increasing in a transplant recipient over time, then the cells of the allograft are increasingly experiencing apoptosis and/or necrosis over time, which is indicative of transplant rejection.

In some embodiments, a decrease in the levels or variance of the donor-derived cell-free DNA in the transplant recipient over time is indicative of transplant tolerance, a need for adjusting immunosuppressive therapy, and/or a need for further investigation of the allograft status. Without wishing to be bound by theory, it is believed that if the level of donor-derived cell-free DNA is decreasing in a transplant recipient over time, then the cells of the allograft are decreasingly experiencing apoptosis and/or necrosis over time, which is indicative of transplant tolerance, overimmunosuppression, or appropriate immunosuppression.

In some embodiments, no change in the levels or variance of the donor-derived cell-free DNA in the transplant recipient over time is indicative of stable transplant rejection status and/or opportunity for adjusting immunosuppressive therapy. Without wishing to be bound by theory, it is believed that if the level of donor-derived cell-free DNA is not changing in a transplant recipient over time, then the cells of the allograft are experiencing a steady-state level of apoptosis over time, which is indicative of a stable transplant rejection status. A stable transplant rejection status informs the status of the allograft during the time window analyzed, but does not inform the direction, either towards rejection or tolerance, the allograft is progressing toward. For example, the allograft may be undergoing active rejection in the transplant recipient, but a stable transplant rejection status indicates that the rate of allograft rejection is not changing during the time it was analyzed (i.e. the rate of transplant rejection is not increasing or decreasing). Similarly, the allograft may be undergoing active tolerance in the transplant recipient, but a stable transplant rejection status indicates that the rate of allograft tolerance is not changing during the time it was analyzed (i.e. the rate of transplant tolerance is not increasing or decreasing).

Adjustment of Immunosuppressive Therapy

The methods of the present disclosure for determining the levels of donor-derived cell-free DNA in a sample from a transplant recipient can be used to inform the need to adjust immunosuppressive therapy being administered to the transplant recipient. In general, changes in the levels or variance of donor-derived cell-free DNA beyond a suitable threshold value in the transplant recipient over time are informative with regard to determining a need to adjust immunosuppressive therapy being administered to the transplant recipient.

Immunosuppressive therapy generally refers to the administration of an immunosuppressant or other therapeutic agent that suppresses immune responses to a subject. Exemplary immunosuppressant agents may include, for example, anticoagulents, antimalarials, heart drugs, nonsteroidal anti-inflammatory drugs (NSAIDs), and steroids including, for example, Ace inhibitors, aspirin, azathioprine, B7RP-1-fc, β-blockers, brequinar sodium, campath-1H, celecoxib, chloroquine, corticosteroids, coumadin, cyclophosphamide, cyclosporin A, DHEA, deoxyspergualin, dexamethasone, diclofenac, dolobid, etodolac, everolimus, FK778, feldene, fenoprofen, flurbiprofen, heparin, hydralazine, hydroxychloroquine, CTLA-4 or LFA3 immunoglobulin, ibuprofen, indomethacin, ISAtx-247, ketoprofen, ketorolac, leflunomide, meclophenamate, mefenamic acid, mepacrine, 6-mercaptopurine, meloxicam, methotrexate, mizoribine, mycophenolate mofetil, naproxen, oxaprozin, Plaquenil, NOX-100, prednisone, methyprenisone, rapamycin (sirolimus), sulindac, tacrolimus (FK506), thymoglobulin, tolmetin, tresperimus, UO126, and antibodies including, for example, alpha lymphocyte antibodies, adalimumab, anti-CD3, anti-CD25, anti-CD52 anti-IL2R, and anti-TAC antibodies, basiliximab, daclizumab, etanercept, hu5C8, infliximab, OKT4, and natalizumab.

In some embodiments, an increase in the levels or variance of the donor-derived cell-free DNA in the transplant recipient over time is indicative of a need to increase immunosuppressive therapy being administered to the transplant recipient. The decision to increase immunosuppressive therapy being administered to a transplant recipient may be based on additional clinical factors, such as the health of the transplant recipient. In some embodiments, immunosuppressive therapy being administered to the subject is increased.

In some embodiments, a decrease in the levels or variance of the donor-derived cell-free DNA in the transplant recipient over time is indicative of a need to decrease immunosuppressive therapy being administered to the transplant recipient. The decision to decrease immunosuppressive therapy being administered to a transplant recipient may be based on additional clinical factors, such as the health of the transplant recipient. In some embodiments, immunosuppressive therapy being administered to the subject is decreased.

In some embodiments, no change in the levels or variance of the donor-derived cell-free DNA in the transplant recipient over time is indicative of no need to adjust immunosuppressive therapy being administered to the transplant recipient, or that the immunosuppressive therapy being administered may be maintained. The decision to maintain immunosuppressive therapy being administered to a transplant recipient may be based on additional clinical factors, such as the health of the transplant recipient. In some embodiments, immunosuppressive therapy being administered to the subject is maintained.

In some embodiments, adjustment of immunosuppressive therapy includes changing the type or form of immunosuppressant or other immunosuppressive therapy being administered to the transplant recipient. In some embodiments where the transplant recipient is not receiving immunosuppressive therapy, the methods of the present disclosure may indicate a need to begin administering immunosuppressive therapy to the transplant recipient.

It should be noted that the levels of donor-derived cell-free DNA in the transplant recipient may not be the only factor taken into consideration when determining a need or lack thereof to adjust an immunosuppressive therapy being administered to the transplant recipient. For example, for a transplant recipient exhibiting both increasing levels of donor-derived cell-free DNA over a time interval and increasing severity of an infection, it may not be advisable to increase or even maintain the current immunosuppressive therapy. It should thus be noted that immunosuppressive therapy being administered to a transplant recipient may be increased, decreased, or maintained irrespective of the determined levels of donor-derived cell-free DNA in the transplant recipient depending on the presence or absence of other controlling clinical factors.

Additional Analyses

The methods of the present disclosure may be performed in addition to or in conjunction with other analyses of samples from a transplant recipient to diagnose the status of the allograft and/or to inform the need to adjust immunosuppressive therapy being administered to the subject.

In some embodiments, the presence or levels of an infectious agent in the transplant recipient is tested. Infectious agents which may be tested for include, for example, viruses; bacteria such as *Pseudomonas aeruginosa, Enterobacteriaceae, Nocardia, Streptococcus pneumonia, Staphyloccous aureus*, and *Legionella*, fungi such as *Candida, Aspergillus, Cryptococcus, Pneumocystis carinii*; or parasites such as *Toxoplasma gondii*.

In some embodiments, the presence or levels of viral infectious agents in the transplant recipient is tested. Viral biomarkers may be analyzed in nucleic acid obtained from a sample from the transplant recipient to determine the presence or levels of viruses in the transplant recipient. Viruses which may be tested for include, for example, Cytomegalovirus, Epstein-Barr virus, Anelloviridae, and BK virus. The results of the tests for presence or levels of viruses may be used to classify the immune status of the transplant recipient and to determine the status of infection in the transplant recipient. In some embodiments, immunosuppressive therapies are decreased, or at least not increased, in transplant recipients that are classified as having a high risk of clinically significant infection. In some embodiments, immunosuppressive therapies are increased, or at least not decreased, in transplant recipients that are classified as having a low risk of clinically significant infection. It should be noted that as other clinical factors may inform decisions to adjust immunosuppressive therapies, a transplant recipient may have immunosuppressive therapy currently being administered to them increased, decreased, or maintained irrespective of the results of tests for presence or levels of viruses and/or classification for risk of clinically significant infection.

In some embodiments, the methods of the present disclosure also involve performing an AlloMap test to aid in determining the status of the allograft in a transplant recipient. AlloMap tests involve performing quantitative real-time polymerase chain reaction (qRT-PCR) assays using RNA that has been isolated from peripheral blood mononuclear cells (PBMC). The expression of a select number of genes is analyzed and this gene expression data is used to provide information relating to the status of an allograft in a transplant recipient. The AlloMap test is known in the art. Results of an AlloMap test may be used in conjunction with the methods of the present disclosure, with or without a method to define a single score from the combined tests, to determine the status of an allograft in a transplant recipient and/or inform the need to adjust immunosuppressive therapy being administered to the transplant recipient.

In some embodiments, the methods of the present disclosure involve determining a combination score that may be used to convey the status of an allograft in a transplant recipient. Combination scores are generally calculated based on the results of multiple (e.g. two or more) assays used to probe the status of the allograft in the transplant recipient. For example, combination scores may be calculated based on the determined levels of donor-derived cell-free DNA in the transplant recipient and based on the results of a gene expression profiling assay such as, for example, an AlloMap test, which measures select gene expression. Combination scores may be calculated based on a single sample taken from a transplant recipient, or they may be based on samples taken from a transplant recipient over a time interval. Combination scores may be used to determine the status of an allograft in a transplant recipient and/or inform the need to adjust immunosuppressive therapy being administered to the transplant recipient.

Additional biomarker analyses, gene expression assays, and other assays for diagnosing the status of an allograft in a transplant recipient and/or determining need to adjust immunosuppressive therapy may also be used in addition to or in conjunction with the methods of the present disclosure, with or without a method to define a single score from the combined tests, which will be readily apparent to one of skill in the art.

Additional analysis may be performed to identify markers of new, metastatic, or recurrent cancers in transplant recipients. Primers may be designed to amplify regions where genetic mutations are known to occur to provide an early detection of cancer by identification of known tumor-associated mutations. This may be advantageous at least in part because transplant recipients may be at heightened risk of developing certain malignancies due to overimmunosuppression.

The following Examples are offered to illustrate provided embodiments and are not intended to limit the scope of the present disclosure.

EXAMPLES

Example 1—Analysis of Cell-Free DNA to Determine Status of Transplanted Organ in a Transplant Recipient and Determine Need to Adjust Immunosuppressive Therapy This Example demonstrates analysis of samples containing cell-free DNA from a transplant recipient to determine the level of donor-derived cell-free DNA in the samples. Changes in the levels of or variance in the donor-derived cell-free DNA over time are used to diagnose the status of the transplanted organ in the transplant recipient, as well as inform the need to adjust or maintain immunosuppressive therapies being administered to the transplant recipient.

Subject Selection

A human patient is selected who was the subject of a kidney transplant 12 months prior to this assay as described in this Example. The patient is undergoing treatment with immunosuppressive therapy to prevent rejection of the allograft. Separate plasma samples will be collected from this subject on a weekly basis over the course of three consecutive months, starting at month 12 (the one year anniversary) after the transplant event. Accordingly, the transplant recipient will be analyzed during months 12, 13, and 14 after the transplant event. The methods described in this Example are applicable to one or more of the samples isolated from the transplant recipient.

Plasma Collection

Blood is extracted from the subject so that cell-free DNA can be extracted from plasma isolated from this blood sample. The blood sample is collected in a cell-free DNA blood collection tube (Streck) according to the venipuncture method as previously described (Clinical and Laboratory Standards Institute, 2012). The Streck tube is filled completely with the blood sample. The tube is removed from the adapter and is immediately mixed by gentle inversion about 8 to 10 times. After collection, the tubes are transported and stored within the temperature range of 6-37° C. for up to 14 days. Upon processing of the sample, the Streck tube containing the blood sample is centrifuged at 1600×g for 20 minutes at room temperature. The resulting plasma layer is carefully removed and is transferred to a 15 mL tube. This plasma sample is then centrifuged at 1600×g for 10 minutes at room temperature. The resulting plasma layer is carefully removed and placed into a new tube, and the plasma sample may then proceed to have cell-free DNA (cf DNA) extracted. PPT plasma preparation tubes (Becton Dickinson) and CPT pour-off methods may also be used during plasma collection.

Cell-Free DNA (cfDNA) Extraction

Approximately 5 mLs of plasma from the plasma sample are used to proceed with cell-free DNA extraction. For cell-free DNA blood collection tubes (Streck), page 26 of the Qiagen protocol (QIAamp Circulating Nucleic Acid Handbook, 2011) may be used with the following modifications: at step 4 on page 28, the incubation period is 1 hour at 60° C., and step 15 on page 29, elute with 30 µL Buffer AVE. For PPT plasma preparation tubes (Becton Dickinson), page 22 of the Qiagen protocol (QIAamp Circulating Nucleic Acid Handbook, 2011) may be used with the following modifications: at step 15 on page 25, elute with 21 µL Buffer AVE. The QIAsymphony method may also be used to extract cfDNA. Other DNA extraction methods may also include phenol/chloroform-based extraction methods.

SNP Selection

After extraction of cell-free DNA from the subject's plasma sample, various SNPs can be assayed in the cell-free DNA. A variety of SNPs are selected for analysis. SNPs may be selected based on those that can provide the highest possible minor allele frequencies (nearest to 50%). The location of the SNPs in the subject's genome may vary; genetic linkage may be allowed, but some genetic separation of the SNPs such as, for example, >200 bp separation may also be desirable. The number and identity of SNPs to be used should provide sufficient power to accurately estimate the percentage of donor-derived cfDNA present in the subject's plasma sample. The SNPs to be used in this assay include those previously identified (Pakstis et al., 2010). To amplify the SNPs, 92 primer pairs are designed (Fluidigm).

Materials for DNA Amplification

To amplify targeted regions which include SNPs of interest in the cell-free DNA, various materials are assembled which will be used in the amplification process. The Fast-Start High Fidelity PCR System (Roche) will be used. 92 primer pairs are designed and produced (IDT or Fluidigm per Fluidgim design). ExoI and ExoI buffer (New England BioLabs) will be used. Methods to follow include the Fluidigm pre-amplification protocol (See Page 152 of Access Array System for Illumina Sequencing System). Instruments that will be used include a PCR machine, a plate centrifuge, and a vortexer.

DNA Amplification

The cell-free DNA is amplified according to the Fluidigm Access Array process and protocols (See page 63 of Access Array System for Illumina Sequencing System). Materials to be used for this amplification protocol include a Fluidigm Access Array, or chip, FastStart High Fidelity PCR system (Roche), 1× Access Array Harvest Solution (Fluidigm, PN 100-1031), 20× Access Array Loading reagent (Fluidigm), and the 92 primer pairs designed as described above. Instruments to be used for this amplification protocol include two IFC Controller AX (Fluidigm) and one FC1 cycler (Fluidigm).

Barcoding

After cell-free DNA is amplified, the amplified DNA is barcoded. Barcoding may be done, for example, to uniquely identify which of the three samples any detected amplified DNA originated from if cell-free DNA molecules from all of the samples are to be sequenced together. The amplified cell-free DNA is barcoded according to the Fluidigm Access Array process and protocols (See page 70 of Access Array System for Illumina Sequencing System). Materials to be used for this barcoding protocol include a FastStart High Fidelity PCR system (Roche), and an Access Array Barcode Library for Illumina Sequencers (Fluidigm). Instruments that will be used include a PCR machine, a plate centrifuge, and a vortexer.

Sequencing

After the cell-free DNA has been barcoded, it is sequenced. The barcoded cell-free DNA is sequenced according to Fluidigm/Illumina sequencing protocols for multiplex sequencing (See page 134 of Access Array System for Illumina Sequencing System). Materials to be used for this sequencing protocol include FL1 and FL2 sequencing primers (Fluidigm), HT1 buffer (Illumina), and a MiSeq Reagent Kit v2 (Illumina). Instruments that will be used include a MiSeq sequencing instrument (Illumina).

Data Analysis

After the cell-free DNA is sequenced, it is analyzed to determine the presence and/or quantity of various SNP alleles as described above. Primary analysis involves the generation of FASTQ output files from the MiSeq instrument. Secondary analysis involves alignment of the output sequences sequenced by MiSeq to a reference sequence, which in this case will be sequences from the human genome. The alignment software "Bowtie" is used to conduct the alignment to the whole genome using default settings. If desired, modifications can be made so that only the intended amplicons are aligned. Allele-aware aligners may also be used to achieve better alignment to non-reference alleles (50% of alignments). After alignment is complete, variant frequencies are assigned using the "LoFreq" software program (Wilm et al., 2012). Tertiary analysis involves quality control aspects of the analysis. Data is analyzed to ensure that the minimum number of reads have been reached to achieve sufficient counting. Data is also analyzed to ensure that the minimum number of SNP loci above background and below the heterozygous call level has been reached. These lower (background) and upper (transplant recipient heterozygous loci) limits may vary. Further, genomic DNA may be determined and a cutoff assigned.

Methods used in the tertiary data will determine the levels of donor-derived cell-free DNA in a given sample. The analysis will include determining low and high cutoff values, assigning values to homozygous and heterozygous SNPs, multiplying heterozygous SNPs by 2, calculating the median, and calculating the confidence interval (CI). Additional analysis methods and/or methods to improve analysis quality include likelihood-based determinations of the contribution of each allele, use of control DNA in each sequencing reaction with defined noise levels per locus, assigning homozygous or heterozygous status based on likelihood or β-distributions, and assigning calls that are potentially weighted to deal with compression artifacts at the low end. It is noted that each additional sample from a subject may improve the confidence in the accuracy of determining the percentage of donor-derived cell-free DNA.

Determining Status of the Transplanted Organ

The data analysis methods described above are used to determine the level of donor-derived cell-free DNA in each of the cell-free DNA samples obtained from the transplant recipient. The data analysis involves comparison of the levels of donor-derived cell-free DNA in each of the three samples to determine if the levels of donor-derived cell-free DNA is increasing, decreasing, or is being maintained at relatively constant levels in cell-free DNA isolated from the transplant recipient over time. An increase in the levels or variance of the donor-derived cell-free DNA over time is indicative of transplant rejection, a need for adjusting immunosuppressive therapy, and/or a need for further investigation of the transplanted organ status. A decrease in the levels or variance of the donor-derived cell-free DNA over time is indicative of transplant tolerance, a need for adjusting immunosuppressive therapy, and/or a need for further investigation of the transplanted organ status. No change in the levels or variance of the donor-derived cell-free DNA over time is indicative of stable transplant rejection status and/or an opportunity for adjusting immunosuppressive therapy.

Example 2—Additional Analysis of Cell-Free DNA to Determine Status of Transplanted Organ in a Transplant Recipient and Determine Need to Adjust Immunosuppressive Therapy This Example demonstrates additional analysis of samples containing cell-free DNA from a transplant recipient to determine the level of donor-derived cell-free DNA in the samples that builds upon the analysis described in Example 1. Changes in the levels of or variance in the donor-derived cell-free DNA over time are used to diagnose the status of the transplanted organ in the transplant recipient, as well as inform the need to adjust or maintain immunosuppressive therapies being administered to the transplant recipient.

Subject Selection

A human patient is selected who was the subject of a kidney transplant 12 months prior to this assay as described in this Example. The patient is undergoing treatment with immunosuppressive therapy to prevent rejection of the allograft. Separate plasma samples will be collected from this subject on a weekly basis over the course of three consecutive months, starting at month 12 (the one year anniversary) after the transplant event. Accordingly, the transplant recipient will be analyzed during months 12, 13, and 14 after the transplant event. The methods described in this Example are applicable to one or more of the samples isolated from the transplant recipient.

Plasma Collection

Blood is extracted from the subject so that cell-free DNA can be extracted from plasma isolated from this blood sample. The blood sample is collected in a cell-free DNA blood collection tube (Streck cell-free DNA BCT) according to the venipuncture method as previously described (Clinical and Laboratory Standards Institute, 2012). The Streck tube is filled completely with the blood sample. The tube is removed from the adapter and is immediately mixed by gentle inversion about 8 to 10 times. After collection, the tubes are transported and stored within the temperature range of 6-37° C. for up to 14 days. Upon processing of the sample, the Streck tube containing the blood sample is centrifuged at 1600×g for 20 minutes at room temperature. The resulting plasma layer is carefully removed and is transferred to a 15 mL tube. This plasma sample is then centrifuged at 1600×g for 10 minutes at room temperature, the supernatant removed and placed into a new tube and centrifuged at 16,000×g for 10 minutes at room temperature. The resulting plasma layer is carefully removed and placed into a new tube, and the plasma sample may then proceed to have cell-free DNA (cfDNA) extracted. PPT plasma preparation tubes (Becton Dickinson) and CPT pour-off methods may also be used during plasma collection.

Cell-Free DNA (cfDNA) Extraction

Approximately 5 mLs of plasma from the plasma sample are used to proceed with cell-free DNA extraction. For cell-free DNA blood collection tubes (Streck), page 26 of the Qiagen protocol (QIAamp Circulating Nucleic Acid Handbook, 2011) may be used with the following modifications: at step 4 on page 28, the incubation period is 1 hour at 60° C., and step 15 on page 29, elute with 30 µL Buffer AVE. For PPT plasma preparation tubes (Becton Dickinson), page 22 of the Qiagen protocol (QIAamp Circulating Nucleic Acid Handbook, 2011) may be used with the following modifications: at step 15 on page 25, elute with 21 µL Buffer AVE. The QIAsymphony methods may also be used to extract cfDNA. Other DNA extraction methods may also include phenol/chloroform-based extraction methods.

SNP Selection

After extraction of cell-free DNA from the subject's plasma sample, various SNPs can be assayed in the cell-free DNA. A variety of SNPs are selected for analysis. SNPs may be selected based on those that can provide the highest possible minor allele frequencies (nearest to 50%). The location of the SNPs in the subject's genome may vary; genetic linkage may be allowed, but some genetic separation of the SNPs such as, for example, >200 bp separation may also be desirable. The number and identity of SNPs to be used should provide sufficient power to accurately estimate the percentage of donor-derived cfDNA present in the subject's plasma sample. The SNPs to be used in this assay include those previously identified (Pakstis et al., 2010), as well as others selected to meet the greater than 0.4 minor allele frequency, an established low rate of DNA polymerase error, and low linkage. To amplify the SNPs, 266 primer pairs are designed (Fluidigm).

DNA Pre-Amplification

To amplify targeted regions which include SNPs of interest in the cell-free DNA, various materials are assembled which will be used in the amplification process. A high-fidelity polymerase such as FastStart High Fidelity (Roche), Expand High Fidelity (Roche), Phusion Flash II (ThermoFisher Scientific), Phusion Hot Start II (ThermoFisher Scientific), KAPA HiFi (Kapa BioSystems), or KAPA2G (Kapa Biosystems) will be used. 266 primer pairs are designed and produced (IDT or Fluidigm per Fluidgim design). ExoI and ExoI buffer (New England BioLabs) will be used. Methods to follow include the Fluidigm pre-amplification protocol (See Page 152 of Access Array System for Illumina Sequencing System). Instruments that will be used include a PCR machine, a plate centrifuge, and a vortexer.

DNA Amplification

The cell-free DNA is amplified according to the Fluidigm Access Array process and protocols (See page 63 of Access Array System for Illumina Sequencing System). Materials to be used for this amplification protocol include a Fluidigm Access Array, or chip, a high-fidelity polymerase such as FastStart High Fidelity (Roche), Expand High Fidelity (Roche), Phusion Flash II (ThermoFisher Scientific), Phusion Hot Start II (ThermoFisher Scientific), KAPA HiFi (Kapa BioSystems), or KAPA2G (Kapa Biosystems), 1× Access Array Harvest Solution (Fluidigm, PN 100-1031), 20× Access Array Loading reagent (Fluidigm), and the 226 primer pairs designed as described above. Instruments to be used for this amplification protocol include two IFC Controller AX (Fluidigm) and one FC1 cycler (Fluidigm).

Indexing (Also Known as Barcoding)

After cell-free DNA is amplified, the amplified DNA is indexed using index sequences, also called barcodes or tags. Indexing may be done, for example, to uniquely identify which of the three samples any detected amplified DNA originated from if cell-free DNA molecules from all of the samples are to be sequenced together. The amplified cell-free DNA is indexed according to the Fluidigm Access Array process and protocols (See page 70 of Access Array System for Illumina Sequencing System). Materials to be used for this indexing protocol include a high-fidelity polymerase such as FastStart High Fidelity (Roche), Expand High Fidelity (Roche), Phusion Flash II (ThermoFisher Scientific), Phusion Hot Start II (ThermoFisher Scientific), KAPA HiFi (Kapa BioSystems), or KAPA2G (Kapa Biosystems), and an Access Array Barcode Library for Illumina Sequencers (Fluidigm—also called an index library). Instruments that will be used include a PCR machine, a plate centrifuge, and a vortexer.

Sequencing

After the cell-free DNA has been amplified and indexed, it is sequenced. The indexed cell-free DNA is sequenced according to Fluidigm/Illumina sequencing protocols for multiplex sequencing (See page 134 of Access Array System for Illumina Sequencing System). Materials to be used for this sequencing protocol include FL1 and FL2 sequencing primers (Fluidigm), HT1 buffer (Illumina), and a MiSeq Reagent Kit v3 (Illumina). Instruments that will be used include a MiSeq sequencing instrument (Illumina).

Data Analysis

Figure 7:
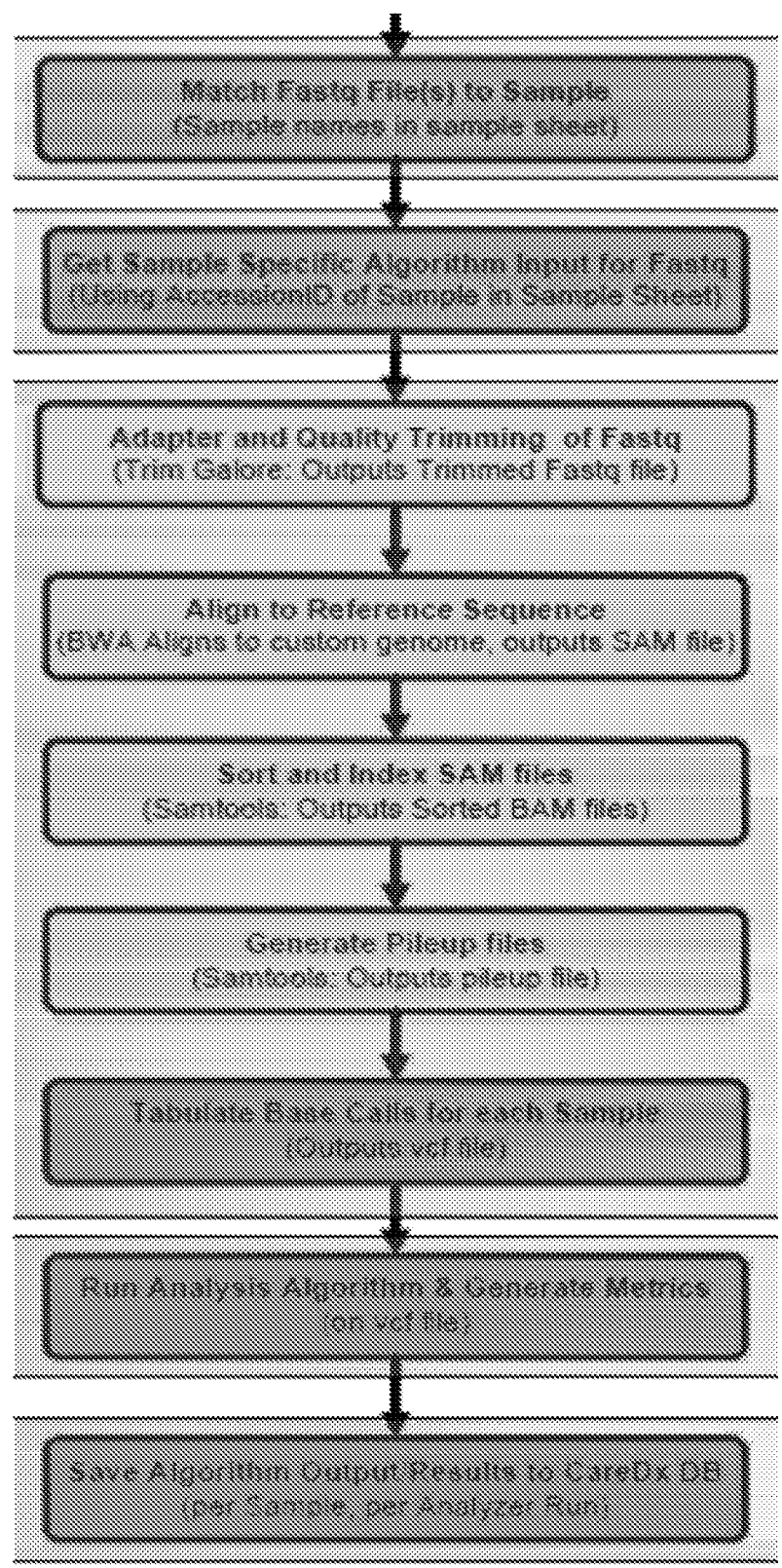
FIG. 7 illustrates an exemplary workflow of the polymorphic marker analysis methods described herein.

After the cell-free DNA is sequenced, it is analyzed to determine the presence and/or quantity of various SNP alleles as described above (See e.g. FIG. 7). Primary analysis involves the generation of FASTQ output files from the MiSeq instrument. Secondary analysis involves alignment of the output sequences sequenced by MiSeq to a reference sequence, which in this case will be sequences from the human genome. End trimming happens using the "Cutadapt" and "TrimGalore" software packages. The alignment software "BWA" is used to conduct the alignment to the genomic regions encompassing the set of amplified amplicons. Allele-aware aligners may also be used to achieve better alignment to non-reference alleles (50% of alignments). After alignment is complete, variant frequencies are assigned using the "SAMtools" software program and settings customized to minimize inclusion of sequencing errors. Tertiary analysis involves quality control aspects of the analysis. Data is analyzed to ensure that the minimum number of reads have been reached to achieve sufficient counting for each SNP position and ensure that there are not additional alleles present in the recipient. Data is also analyzed to ensure that the minimum and maximum number of SNP loci above background and below the heterozygous call level has been reached. These lower (background) and upper (transplant recipient heterozygous loci) limits may vary. In addition, there are metrics to ensure sufficient input DNA to achieve accurate measurement by determining the quality of the heterozygous SNP data. Further, genomic DNA may be determined and a cutoff assigned.

Methods used in the tertiary data will determine the levels of donor-derived cell-free DNA in a given sample. The analysis includes determining the set of SNPs that are homozygous in the recipient, determining low and high cutoff values for the allele frequency of the recipient homozygous SNPs to use in estimating the percent donor-derived cell-free DNA, computing the mean of the remaining homozygous recipient SNPs, and assessing a multiplier based on the relationship between the donor and recipient, and calculating the confidence interval (CI). Additional analysis methods and/or methods to improve analysis quality include likelihood- or Bayesian-based estimates of the donor or recipient allele distributions for each SNP or of the percent donor-derived cell free DNA, and use of control DNA in each sequencing reaction with defined noise levels per locus. It is noted that each additional sample from a subject may improve the confidence in the accuracy of determining the percentage of donor-derived cell-free DNA.

Determining Status of the Transplanted Organ

The data analysis methods described above are used to determine the level of donor-derived cell-free DNA in each of the cell-free DNA samples obtained from the transplant recipient. The data analysis involves comparison of the levels of donor-derived cell-free DNA in each of the three samples to determine if the levels of donor-derived cell-free DNA is increasing, decreasing, or is being maintained at relatively constant levels in cell-free DNA isolated from the transplant recipient over time. An increase in the levels or variance of the donor-derived cell-free DNA over time is indicative of transplant rejection, a need for adjusting immunosuppressive therapy, and/or a need for further investigation of the transplanted organ status. A decrease in the levels or variance of the donor-derived cell-free DNA over time is indicative of transplant tolerance, a need for adjusting immunosuppressive therapy, and/or a need for further investigation of the transplanted organ status. No change in the levels or variance of the donor-derived cell-free DNA over time is indicative of stable transplant rejection status and/or an opportunity for adjusting immunosuppressive therapy.

Example 3—Analysis of Cell-Free DNA to Determine Status of Transplanted Organ in a Heart Transplant Recipient and Predict Need to Adjust Immunosuppressive Therapy This Example demonstrates analysis of samples containing cell-free DNA from a set of 18 transplant recipients to determine the level of donor-derived cell-free DNA in the samples. Changes in the levels of donor-derived cell-free DNA over time are used to diagnose the status of the transplanted organ in the transplant recipient and predict future status of the transplanted organ, as well as inform the need to adjust or maintain immunosuppressive therapies being administered to the transplant recipient.

Subject Selection

Human patients were selected who were the subject of a heart transplants prior to this assay as described in this Example. The patients were undergoing treatment with immunosuppressive therapy to prevent rejection of the allograft. Separate plasma samples were collected from these subjects at visits dictated by the standard of care at their respective centers over the course of five consecutive months. The methods described in this Example are applicable to one or more of the samples isolated from the transplant recipient.

Plasma Collection

Blood was extracted from the subjects so that cell-free DNA could be extracted from plasma isolated from the blood sample. The blood sample was collected in PPT tubes according to the venipuncture method as previously described (Clinical and Laboratory Standards Institute, 2012). The PPT tube (Plasma Preparation Tube, Becton Dickinson) was filled completely with the blood sample. The tube was removed from the adapter and immediately mixed by gentle inversion. After collection, the tubes were centrifuged according to the manufacturer's protocol and stored at −80° C. Upon processing of the sample, the tube was thawed and the plasma layer was carefully removed and transferred to a clean tube. The plasma sample was then centrifuged at 1600×g for 10 minutes at room temperature, the supernatant removed and placed into a new tube and centrifuged at 16,000×g for 10 minutes at room temperature. The resulting plasma layer was carefully removed and placed into a new tube in preparation to have cell-free DNA (cf DNA) extracted.

Cell-Free DNA (cfDNA) Extraction

Approximately 1 mL of plasma from the plasma sample was used to proceed with cell-free DNA extraction. For PPT plasma preparation tubes (Becton Dickinson), page 22 of the Qiagen protocol (QIAamp Circulating Nucleic Acid Handbook, 2011) was used with the following modifications: at step 15 on page 25, elute with 21 µL Buffer AVE.

SNP Selection

Various SNPs were selected for analysis to estimate the percentage of donor-derived cfDNA present in the subject's plasma sample. The SNPs selected for analysis were rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. To amplify the SNPs, 266 primer pairs were designed (Fluidigm).

DNA Pre-Amplification

To amplify targeted regions which include SNPs of interest in the cell-free DNA, various materials were assembled and used in the amplification process. The Phusion Hot Start II DNA Polymerase (ThermoFisher Scientific) was used. 266 primer pairs were designed and produced (IDT or Fluidigm per Fluidgim design). ExoI and ExoI buffer (New England BioLabs) were used. Methods followed included the Fluidigm pre-amplification protocol (See Page 152 of Access Array System for Illumina Sequencing System). Instruments used included a PCR machine, a plate centrifuge, and a vortexer.

DNA Amplification

The cell-free DNA from the pre-amplification was amplified according to the Fluidigm Access Array process and protocols (See page 63 of Access Array System for Illumina Sequencing System). Materials used for this amplification protocol included a Fluidigm Access Array, or chip, the high-fidelity DNA polymerase Phusion Flash II (ThermoFisher Scientific), 1× Access Array Harvest Solution (Fluidigm, PN 100-1031), 20× Access Array Loading reagent (Fluidigm), and the 266 primer pairs designed as described above. Instruments used for this amplification protocol included two IFC Controller AX (Fluidigm) and one FC1 cycler (Fluidigm).

Indexing (Also Known as Barcoding)

After cell-free DNA was amplified, the amplified DNA was indexed using index sequences, also called barcodes or tags. Indexing may be done, for example, to uniquely identify which of the three samples any detected amplified DNA originated from if cell-free DNA molecules from all of the samples are to be sequenced together. The amplified cell-free DNA was indexed according to the Fluidigm Access Array process and protocols (See page 70 of Access Array System for Illumina Sequencing System). Materials used for this indexing protocol included the high-fidelity polymerase Phusion Hot Start II (ThermoFisher Scientific), and an Access Array Barcode Library for Illumina Sequencers (Fluidigm—also called an index library). Instruments used included a PCR machine, a plate centrifuge, and a vortexer.

Sequencing

After the cell-free DNA was amplified and indexed, it was sequenced. The indexed cell-free DNA was sequenced according to Fluidigm/Illumina sequencing protocols for multiplex sequencing (See page 134 of Access Array System for Illumina Sequencing System). Materials used for this sequencing protocol included FL1 and FL2 sequencing primers (Fluidigm), HT1 buffer (Illumina), and a MiSeq Reagent Kit v3 (Illumina). Cell-free DNA was sequenced using a MiSeq sequencing instrument (Illumina).

Data Analysis

After the cell-free DNA was sequenced, it was analyzed to determine the presence and/or quantity of various SNP alleles (See FIG. 7 for general outline). Primary analysis involved the generation of FASTQ output files from the MiSeq instrument. Secondary analysis involved alignment of the output sequences sequenced by MiSeq to the human genome reference sequence. End trimming was performed using the "Cutadapt" and "TrimGalore" software packages. The alignment software "BWA" was used to conduct the alignment to the genomic regions encompassing the set of amplified amplicons. After alignment was complete, variant frequencies were assigned using the "SAMtools" software program and settings customized to minimize inclusion of sequencing errors.

Tertiary analysis of this type of data generally involves quality control aspects of the analysis. Data is analyzed to ensure that the minimum number of reads have been reached to achieve sufficient counting for each SNP position and ensure that there are not additional alleles present in the recipient. Data is also analyzed to ensure that the minimum and maximum number of SNP loci above background and below the heterozygous call level has been reached. These lower (background) and upper (transplant recipient heterozygous loci) limits may vary. In addition, there are metrics to ensure sufficient input DNA to achieve accurate measurement by determining the quality of the heterozygous SNP data. Further, genomic DNA may be determined and a cutoff assigned.

Methods used in the tertiary data determined the levels of donor-derived cell-free DNA in a given sample. The analysis included adjusting the minor allele frequency of the SNPs for sequencing or amplification errors by subtracting an empirically determined error rate for each transition or transversion, determining the set of SNPs that have a minor allele frequency lower than a cutoff between 0.1 to 0.25 as homozygous in the recipient, then using the level of the minor allele in these SNPs for calculation of donor contribution as a percent of the total cell-free DNA. SNPs with values less than 0.0008 minor allele frequency were removed. The median of the lower 55.4% of the remaining SNPs was doubled and averaged with the median of the highest 44.6% of the SNPs to estimate the donor contribution.

Determining Status of the Transplanted Organ

Figure 2:
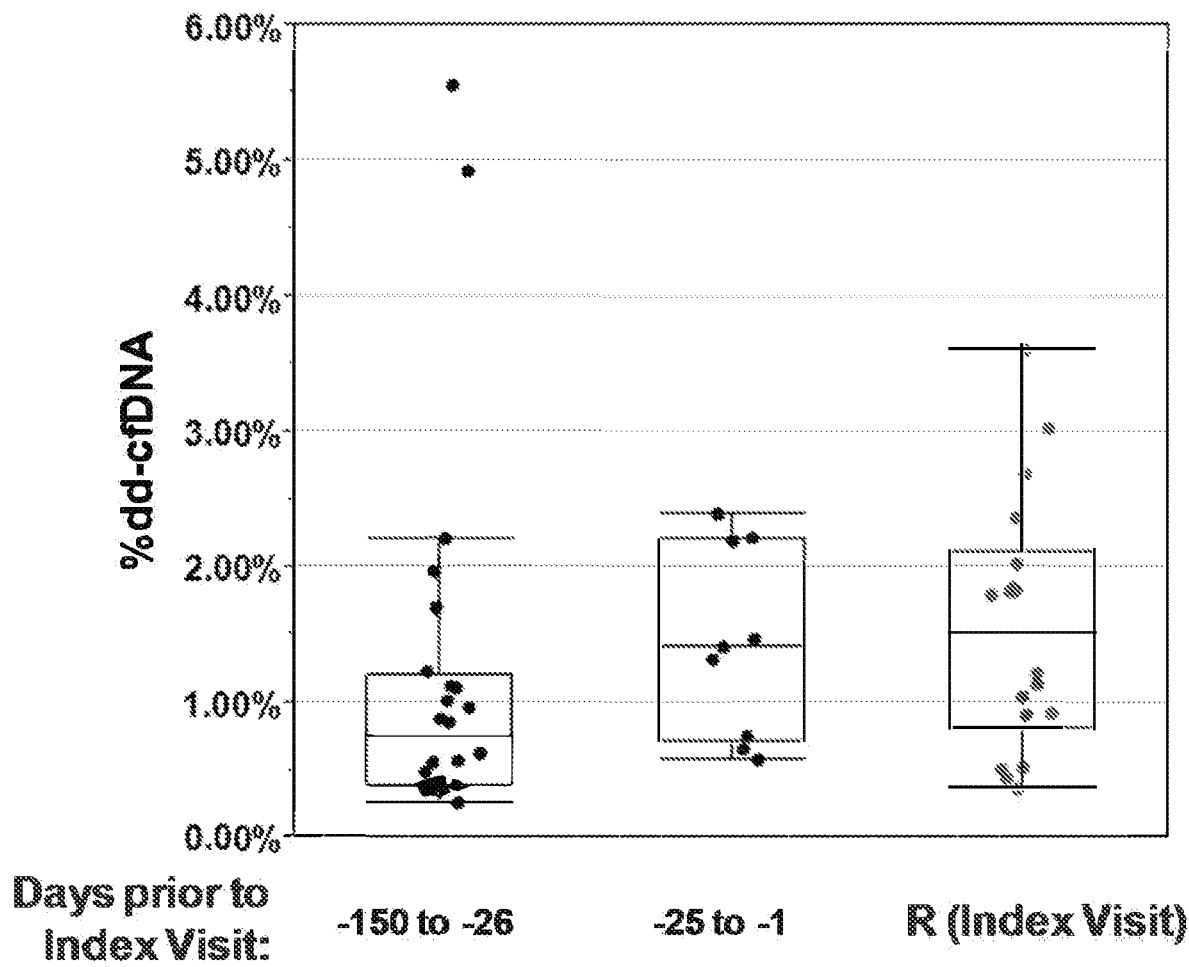
FIG. 2 illustrates that dd-cfDNA is elevated prior to heart transplant rejection. Data was generated using plasma from heart transplant recipients collected in PPT tubes. Patient samples were assigned R (rejection) status based on the status of endomyocardial biopsy performed at the same patient visit. Visits prior to the rejection event were grouped according to the time prior to the rejection visit (25 for fewer days or longer than 25 days). Donor-derived cell-free DNA is expressed as a percent of the total cell-free DNA, measured as described herein.

The data analysis methods described above were used to determine the level of donor-derived cell-free DNA in each of the cell-free DNA samples obtained from the transplant recipients. The data analysis involved comparison of the levels of donor-derived cell-free DNA in each of the samples to the other samples from that patient to determine if the levels of donor-derived cell-free DNA were increasing, decreasing, or were being maintained at relatively constant levels in cell-free DNA isolated from the transplant recipient over time. An increase in the levels or variance of the donor-derived cell-free DNA over time is indicative of transplant rejection as shown in FIG. 1 and FIG. 2. FIG. 1 shows the relationship between well-characterized rejection and high percent donor-derived cell-free DNA. FIG. 2 shows the ability of elevated cell-free DNA to predict impending rejection within approximately one month. This suggests that the physician may need to adjust immunosuppressive therapy, and/or further investigate the transplanted organ status.

Example 4—Analysis of Cell-Free DNA to Determine Status of Transplanted Organ in a Transplant Recipient, Adjust Immunosuppressive Therapy, and Monitor Treatment This Example demonstrates the analysis of samples containing cell-free DNA from a heart transplant recipient and determination of the level of donor-derived cell-free DNA in the samples. The levels of the donor-derived cell-free DNA are used to diagnose the status of the transplanted organ in the transplant recipient, as well as inform the need to adjust or maintain immunosuppressive therapies being administered to the transplant recipient. Ongoing changes in the levels of donor-derived cell-free DNA may be subsequently used to monitor success of the changes in immunosuppressive therapy.

Subject Selection

A human patient was selected who was the subject of a heart transplant prior to this assay as described in this Example. The patient was undergoing treatment with immunosuppressive therapy to prevent rejection of the allograft. Separate plasma samples were collected at regular visits according to the standard of care within the three months following rejection. Accordingly, the transplant recipient was analyzed during the weeks following a rejection event. The methods described in this Example are applicable to one or more of the samples isolated from the transplant recipient.

Plasma Collection

Blood was extracted from the subject so that cell-free DNA could be extracted from plasma isolated from the blood sample. The blood sample was collected in PPT tubes according to the venipuncture method as previously described (Clinical and Laboratory Standards Institute, 2012). The PPT tube (Plasma Preparation Tube, Becton Dickinson) was filled completely with the blood sample. The tube was removed from the adapter and was immediately mixed by gentle inversion. After collection, the tubes were centrifuged according to the manufacturer's protocol and stored at −80° C. Upon processing of the sample, the tube was thawed and the plasma layer was carefully removed and transferred to a clean tube. This plasma sample was then centrifuged at 1600×g for 10 minutes at room temperature, the supernatant removed and placed into a new tube and centrifuged at 16,000×g for 10 minutes at room temperature. The resulting plasma layer was carefully removed and placed into a new tube, and the plasma sample proceeded to have cell-free DNA (cf DNA) extracted.

Cell-Free DNA (cfDNA) Extraction

Approximately 1 mL of plasma from the plasma sample was used to proceed with cell-free DNA extraction. For PPT plasma preparation tubes (Becton Dickinson), page 22 of the Qiagen protocol (QIAamp Circulating Nucleic Acid Handbook, 2011) was used with the following modifications: at step 15 on page 25, elute with 21 µL Buffer AVE.

SNP Selection

Various SNPs were selected for analysis to estimate the percentage of donor-derived cfDNA present in the subject's plasma sample. The SNPs selected for analysis were rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. To amplify the SNPs, 266 primer pairs were designed (Fluidigm).

Dna Pre-Amplification

To amplify targeted regions which include SNPs of interest in the cell-free DNA, various materials were assembled and used in the amplification process. The Phusion Hot Start II DNA Polymerase (ThermoFisher Scientific) was used. 266 primer pairs were designed and produced (IDT or Fluidigm per Fluidigm design). ExoI and ExoI buffer (New England BioLabs) were used. Methods followed included the Fluidigm pre-amplification protocol (See Page 152 of Access Array System for Illumina Sequencing System). Instruments used included a PCR machine, a plate centrifuge, and a vortexer.

DNA Amplification

The cell-free DNA from the pre-amplification was amplified according to the Fluidigm Access Array process and protocols (See page 63 of Access Array System for Illumina Sequencing System). Materials used for this amplification protocol included a Fluidigm Access Array, or chip, the high-fidelity DNA polymerase Phusion Flash II (ThermoFisher Scientific), 1× Access Array Harvest Solution (Fluidigm, PN 100-1031), 20× Access Array Loading reagent (Fluidigm), and the 266 primer pairs designed as described above. Instruments used for this amplification protocol included two IFC Controller AX (Fluidigm) and one FC1 cycler (Fluidigm).

Indexing (Also Known as Barcoding)

After cell-free DNA was amplified, the amplified DNA was indexed using index sequences, also called barcodes or tags. Indexing may be done, for example, to uniquely identify which of the three samples any detected amplified DNA originated from if cell-free DNA molecules from all of the samples are to be sequenced together. The amplified cell-free DNA was indexed according to the Fluidigm Access Array process and protocols (See page 70 of Access Array System for Illumina Sequencing System). Materials used for this indexing protocol included the high-fidelity polymerase Phusion Hot Start II (ThermoFisher Scientific), and an Access Array Barcode Library for Illumina Sequencers (Fluidgm—also called an index library). Instruments used included a PCR machine, a plate centrifuge, and a vortexer.

Sequencing

After the cell-free DNA was amplified and indexed, it was sequenced. The indexed cell-free DNA was sequenced according to Fluidigm/Illumina sequencing protocols for multiplex sequencing (See page 134 of Access Array System for Illumina Sequencing System). Materials used for this sequencing protocol included FL1 and FL2 sequencing primers (Fluidigm), HT1 buffer (Illumina), and a MiSeq Reagent Kit v3 (Illumina). Cell-free DNA was sequenced using a MiSeq sequencing instrument (Illumina).

Data Analysis

After the cell-free DNA was sequenced, it was analyzed to determine the presence and/or quantity of various SNP alleles (See FIG. 7 for general outline). Primary analysis involved the generation of FASTQ output files from the MiSeq instrument. Secondary analysis involved alignment of the output sequences sequenced by MiSeq to the human genome reference sequence. End trimming was performed using the "Cutadapt" and "TrimGalore" software packages. The alignment software "BWA" was used to conduct the alignment to the genomic regions encompassing the set of amplified amplicons. After alignment was complete, variant frequencies were assigned using the "SAMtools" software program and settings customized to minimize inclusion of sequencing errors.

Tertiary analysis of this type of data generally involves quality control aspects of the analysis. Data is analyzed to ensure that the minimum number of reads have been reached to achieve sufficient counting for each SNP position and ensure that there are not additional alleles present in the recipient. Data is also analyzed to ensure that the minimum and maximum number of SNP loci above background and below the heterozygous call level has been reached. These lower (background) and upper (transplant recipient heterozygous loci) limits may vary. In addition, there are metrics to ensure sufficient input DNA to achieve accurate measurement by determining the quality of the heterozygous SNP data. Further, genomic DNA may be determined and a cutoff assigned.

Methods used in the tertiary data determined the levels of donor-derived cell-free DNA in a given sample. The analysis included adjusting the minor allele frequency of the SNPs for sequencing or amplification errors by subtracting an empirically determined error rate for each transition or transversion, determining the set of SNPs that have a minor allele frequency lower than a cutoff between 0.1 to 0.25 as homozygous in the recipient, then using the level of the minor allele in these SNPs for calculation of donor contribution as a percent of the total cell-free DNA. SNPs with values less than 0.0008 minor allele frequency were removed. The median of the lower 55.4% of the remaining SNPs was doubled and averaged with the median of the highest 44.6% of the SNPs to estimate the donor contribution.

Determining Status of the Transplanted Organ

Figure 3:
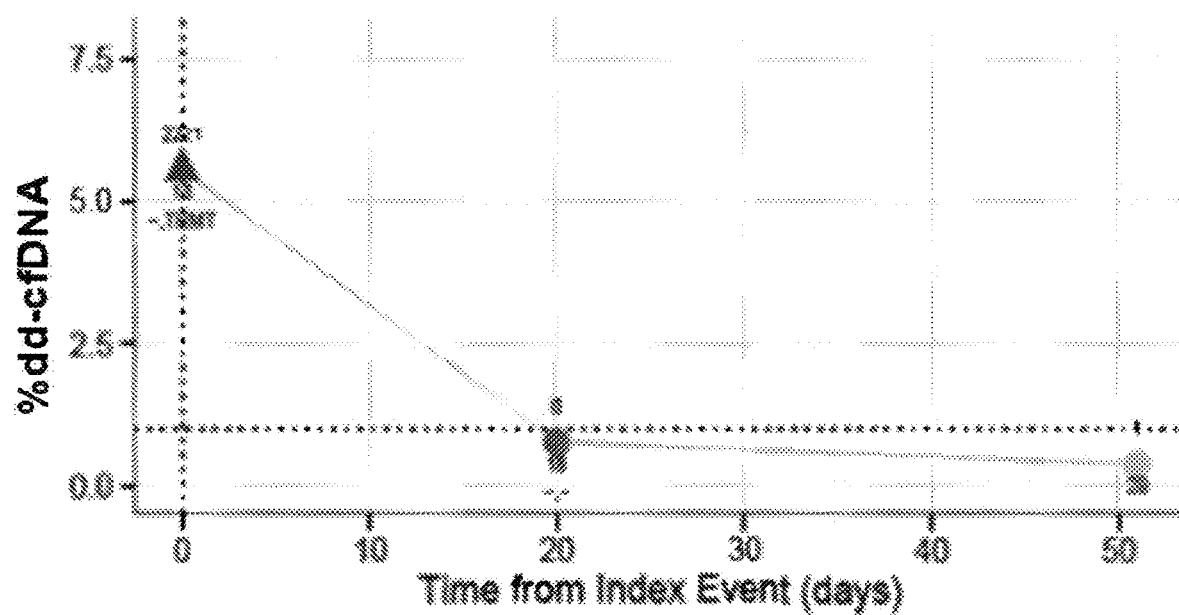
FIG. 3 illustrates that dd-cfDNA is reduced following treatment of heart transplant recipients for acute cellular rejection with increased immunosuppressive therapy. Data was generated using plasma from heart transplant recipients collected in PPT tubes. Patient sample was assigned R (rejection, triangle), or NR (non-rejection, circle) status based on the endomyocardial biopsy performed at the same patient visit. Donor-derived cell-free DNA is expressed as a percent of the total cell-free DNA, measured as described herein. This patient received large-dose immunosuppression with prednisone based on the endomyocardial biopsy status of 2R rejection (index event at 225 days post-transplant).

The data analysis methods described above were used to determine the level of donor-derived cell-free DNA in each of the cell-free DNA samples obtained from the transplant recipient. The data analysis involved comparison of the levels of donor-derived cell-free DNA in each of the samples to the other samples from that patient to determine if the levels of donor-derived cell-free DNA were increasing, decreasing, or were being maintained at relatively constant levels in cell-free DNA isolated from the transplant recipient over time. FIG. 1 shows the relationship between well-characterized rejection and high percent donor-derived cell-free DNA. In this example, as shown in FIG. 3, the patient had experienced rejection (as determined by endomyocardial biopsy) and also had high levels of dd-cfDNA (>5%). The patient was given a bolus steroid immunosuppressive treatment. Subsequent samples taken at 20 and 51 days following treatment demonstrate that successful immunosuppressive treatment can be monitored by examination of dd-cfDNA levels for return to levels that indicate no rejection (FIG. 3).

Example 5—Analysis of Cell-Free DNA to Determine Status of Kidney Transplant in a Transplant Recipient, Adjust Immunosuppressive Therapy, and Monitor Treatment This Example demonstrates the analysis of samples containing cell-free DNA from a kidney transplant recipient to determine the level of donor-derived cell-free DNA in the samples. Changes in the levels of or variance in the donor-derived cell-free DNA over time were used to diagnose the status of the transplanted organ in the transplant recipient, as well as inform the need to adjust or maintain immunosuppressive therapies being administered to the transplant recipient.

Subject Selection

A human patient was selected who was the subject of a kidney transplant 8 days prior to this assay as described in this Example. The patient was undergoing treatment with immunosuppressive therapy to prevent rejection of the allograft. Separate plasma samples were collected from this subject for three consecutive months, starting at the first rejection event 8 days post-transplant. Accordingly, the transplant recipient was analyzed during the weeks following a rejection event. The methods described in this Example are applicable to one or more of the samples isolated from the transplant recipient.

Plasma Collection

Blood was extracted from the subject so that cell-free DNA could be extracted from plasma isolated from the blood sample. The blood sample was collected in CPT tubes according to the venipuncture method as previously described (Clinical and Laboratory Standards Institute, 2012). The CPT tube (Becton Dickinson) was filled completely with the blood sample. The tube was removed from the adapter and was immediately mixed by gentle inversion. After collection, the tubes were centrifuged according to the manufacturer's protocol and the plasma and mononuclear cells fraction was poured off into a tube containing 5 ml PBS. This second tube was centrifuged to pellet the cells and the plasma supernatant was retained and stored at −80° C. Upon processing of the sample, the tube was thawed and the plasma sample was then centrifuged at 1600×g for 10 minutes at room temperature, the supernatant removed and placed into a new tube and centrifuged at 16,000×g for 10 minutes at room temperature. The resulting plasma layer was carefully removed and placed into a new tube, and the plasma sample then proceeded to have cell-free DNA (cfDNA) extracted.

Cell-Free DNA (cfDNA) Extraction

Approximately 1-2 mLs of plasma from the plasma sample was used to proceed with cell-free DNA extraction. For cell-free DNA blood collection tubes (Streck), page 26 of the Qiagen protocol (QIAamp Circulating Nucleic Acid Handbook, 2011) was used with the following modifications: at step 4 on page 28, the incubation period is 1 hour at 60° C., and step 15 on page 29, elute with 30 μL Buffer AVE. For PPT plasma preparation tubes (Becton Dickinson), page 22 of the Qiagen protocol (QIAamp Circulating Nucleic Acid Handbook, 2011) was used with the following modifications: at step 15 on page 25, elute with 21 μL Buffer AVE.

SNP Selection

Various SNPs were selected for analysis to estimate the percentage of donor-derived cfDNA present in the subject's plasma sample. The SNPs selected for analysis were rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. To amplify the SNPs, 266 primer pairs were designed (Fluidigm).

DNA Pre-Amplification

To amplify targeted regions which include SNPs of interest in the cell-free DNA, various materials were assembled and used in the amplification process. The high-fidelity DNA polymerase FastStart High Fidelity (Roche) was used. 266 primer pairs were designed and produced (IDT or Fluidigm per Fluidigm design). ExoI and ExoI buffer (New England BioLabs) were used. Methods followed included the Fluidigm pre-amplification protocol (See Page 152 of Access Array System for Illumina Sequencing System). Instruments used included a PCR machine, a plate centrifuge, and a vortexer.

DNA Amplification

The cell-free DNA from the pre-amplification was amplified according to the Fluidigm Access Array process and protocols (See page 63 of Access Array System for Illumina Sequencing System). Materials used for this amplification protocol included a Fluidigm Access Array, or chip, the high-fidelity DNA polymerase FastStart High Fidelity (Roche), 1× Access Array Harvest Solution (Fluidigm, PN 100-1031), 20× Access Array Loading reagent (Fluidigm), and the 266 primer pairs designed as described above. Instruments used for this amplification protocol included two IFC Controller AX (Fluidigm) and one FC1 cycler (Fluidigm).

Indexing (Also Known as Barcoding)

After cell-free DNA was amplified, the amplified DNA was indexed using index sequences, also called barcodes or tags. Indexing may be done, for example, to uniquely identify which of the three samples any detected amplified DNA originated from if cell-free DNA molecules from all of the samples are to be sequenced together. The amplified cell-free DNA was indexed according to the Fluidigm Access Array process and protocols (See page 70 of Access Array System for Illumina Sequencing System). Materials used for this indexing protocol included the high-fidelity DNA polymerase FastStart High Fidelity (Roche), and an Access Array Barcode Library for Illumina Sequencers (Fluidigm—also called an index library). Instruments used included a PCR machine, a plate centrifuge, and a vortexer.

Sequencing

After the cell-free DNA was amplified and indexed, it was sequenced. The indexed cell-free DNA was sequenced according to Fluidigm/Illumina sequencing protocols for multiplex sequencing (See page 134 of Access Array System for Illumina Sequencing System). Materials used for this sequencing protocol included FL1 and FL2 sequencing primers (Fluidigm), HT1 buffer (Illumina), and a MiSeq Reagent Kit v3 (Illumina). Cell-free DNA was sequenced using a MiSeq sequencing instrument (Illumina).

Data Analysis

After the cell-free DNA was sequenced, it was analyzed to determine the presence and/or quantity of various SNP alleles (See FIG. 7 for general outline). Primary analysis involved the generation of FASTQ output files from the MiSeq instrument. Secondary analysis involved alignment of the output sequences sequenced by MiSeq to the human genome reference sequence. End trimming was performed using the "Cutadapt" and "TrimGalore" software packages. The alignment software "BWA" was used to conduct the alignment to the genomic regions encompassing the set of amplified amplicons. After alignment was complete, variant frequencies were assigned using the "SAMtools" software program and settings customized to minimize inclusion of sequencing errors.

Tertiary analysis of this type of data generally involves quality control aspects of the analysis. Data is analyzed to ensure that the minimum number of reads have been reached to achieve sufficient counting for each SNP position and ensure that there are not additional alleles present in the recipient. Data is also analyzed to ensure that the minimum and maximum number of SNP loci above background and below the heterozygous call level has been reached. These lower (background) and upper (transplant recipient heterozygous loci) limits may vary. In addition, there are metrics to ensure sufficient input DNA to achieve accurate measurement by determining the quality of the heterozygous SNP data. Further, genomic DNA may be determined and a cutoff assigned.

Methods used in the tertiary data determined the levels of donor-derived cell-free DNA in a given sample. The analysis included adjusting the minor allele frequency of the SNPs for sequencing or amplification errors by subtracting an empirically determined error rate for each transition or transversion, determining the set of SNPs that have a minor allele frequency lower than a cutoff between 0.1 to 0.25 as homozygous in the recipient, then using the level of the minor allele for calculation of donor contribution as a percent of the majority allele. The 5% highest and 5% lowest values were removed and the mean of the remaining SNP minor allele values calculated. This value estimates the heterozygous level for the donor contribution, therefore is multiplied by two to determine the final estimate of donor contribution.

Determining Status of the Transplanted Organ

Figure 4:
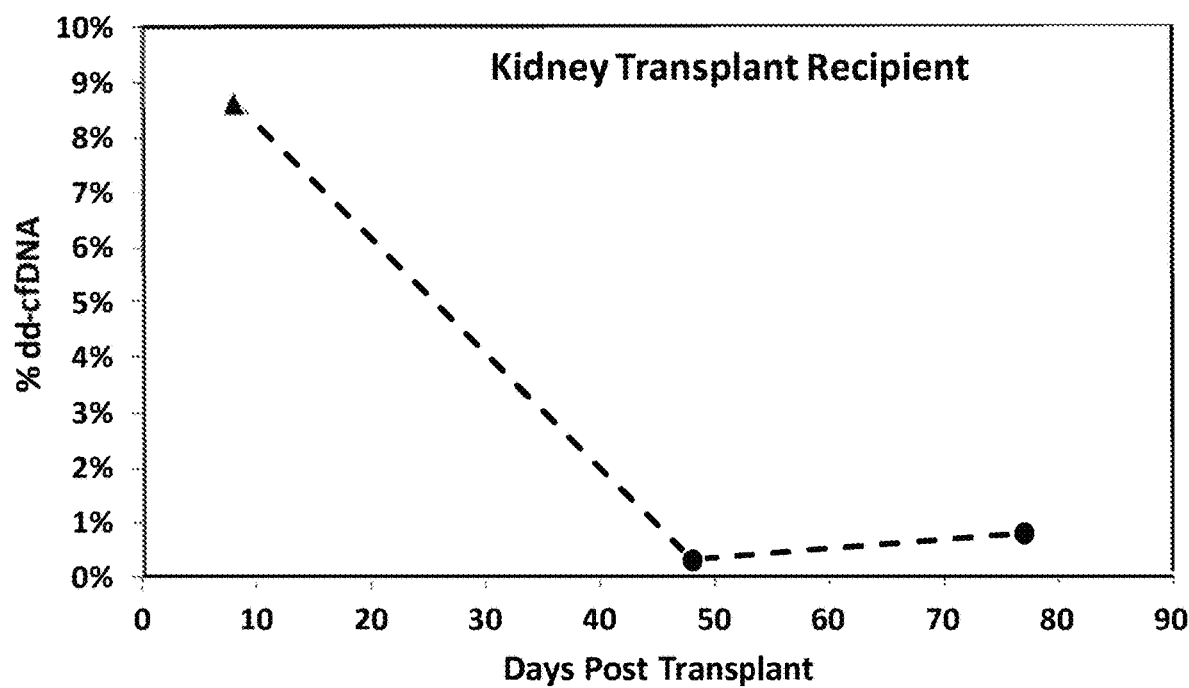
FIG. 4 illustrates that dd-cfDNA is reduced following treatment of kidney transplant recipients for acute cellular rejection with increased immunosuppressive therapy. Data was generated using plasma from kidney transplant recipients collected as supernatant from CPT processing. Patient sample was assigned R (rejection, triangle) based on the biopsy results, NR (non-rejection, circles) based on low serum creatinine and. Donor-derived cell-free DNA is expressed as a percent of the total cell-free DNA, measured as described herein.

The data analysis methods described above were used to determine the level of donor-derived cell-free DNA in each of the cell-free DNA samples obtained from the transplant recipient. The data analysis involved comparison of the levels of donor-derived cell-free DNA in each of the samples to the other samples from that patient to determine if the levels of donor-derived cell-free DNA were increasing, decreasing, or were being maintained at relatively constant levels in cell-free DNA isolated from the transplant recipient over time. FIG. 1 shows the relationship between well-characterized rejection and high percent donor-derived cell-free DNA. In this example, as shown in FIG. 4, the kidney transplant recipient experienced rejection (as determined by renal biopsy) and also had high levels of dd-cfDNA (>8%). The patient was treated by adjustment of immunosuppressive therapy. Subsequent samples taken at 40 and 69 days following treatment demonstrate that successful immunosuppressive treatment can be monitored by examination of dd-cfDNA levels for return to levels that indicate no rejection (less than 1% dd-cfDNA, FIG. 4).

Example 6—Serial Analysis of Cell-Free DNA to Monitor Status of Transplanted Organ in a Transplant Recipient This Example demonstrates the analysis of samples containing cell-free DNA from heart transplant recipients to determine the level of donor-derived cell-free DNA in the samples. Changes in the levels of or variance in the donor-derived cell-free DNA over time were used to diagnose the status of the transplanted organ in a transplant recipient, as well as inform the need to adjust or maintain immunosuppressive therapies being administered to a transplant recipient.

Subject Selection

Human patients were selected who were the subject of a heart transplant prior to this assay as described in this Example. The patients were undergoing treatment with immunosuppressive therapy to prevent rejection of the allograft, but specific treatment information was blinded at the time of testing. Patient selection criteria required that they be stable patients without signs of rejection or other concerns regarding the status of the transplanted organ. Separate plasma samples were collected from these subjects during clinical visits according to standard of care prescribed by the physician. The methods described in this Example are applicable to one or more of the samples isolated from the transplant recipient.

Plasma Collection

Blood was extracted from the subjects so that cell-free DNA could be extracted from plasma isolated from the blood sample. The blood sample was collected in a cell-free DNA blood collection tube (Streck cell-free DNA BCT) according to the venipuncture method as previously described (Clinical and Laboratory Standards Institute, 2012). The Streck tube was filled completely with the blood sample. The tube was removed from the adapter and was immediately mixed by gentle inversion about 8 to 10 times. After collection, the tubes were transported and stored within the temperature range of 6-37° C. for up to 7 days. Upon processing of the sample, the Streck tube containing the blood sample was centrifuged at 1600×g for 20 minutes at room temperature. The resulting plasma layer was carefully removed and was transferred to a 15 mL tube. This plasma sample was then centrifuged at 1600×g for 10 minutes at room temperature, the supernatant removed and placed into a new tube and centrifuged at 16,000×g for 10 minutes at room temperature. The resulting plasma layer was carefully removed and placed into a new tube, and the plasma sample then proceeded to have cell-free DNA (cfDNA) extracted.

Cell-Free DNA (cfDNA) Extraction

Approximately 5 mLs of plasma from the plasma sample was used to proceed with cell-free DNA extraction. For cell-free DNA blood collection tubes (Streck), page 26 of the Qiagen protocol (QIAamp Circulating Nucleic Acid Handbook, 2011) was used with the following modifications: at step 4 on page 28, the incubation period is 1 hour at 60° C., and step 15 on page 29, elute with 30 µL Buffer AVE.

SNP Selection

Various SNPs were selected for analysis to estimate the percentage of donor-derived cfDNA present in the subject's plasma sample. The SNPs selected for analysis were rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. To amplify the SNPs, 266 primer pairs were designed (Fluidigm).

DNA Pre-Amplification

To amplify targeted regions which include SNPs of interest in the cell-free DNA, various materials were assembled and used in the amplification process. The Phusion Hot Start II DNA Polymerase (ThermoFisher Scientific) was used. 266 primer pairs were designed and produced (IDT or Fluidigm per Fluidigm design). ExoI and ExoI buffer (New England BioLabs) were used. Methods followed included the Fluidigm pre-amplification protocol (See Page 152 of Access Array System for Illumina Sequencing System). Instruments used included a PCR machine, a plate centrifuge, and a vortexer.

DNA Amplification

The cell-free DNA from the pre-amplification was amplified according to the Fluidigm Access Array process and protocols (See page 63 of Access Array System for Illumina Sequencing System). Materials used for this amplification protocol included a Fluidigm Access Array, or chip, the high-fidelity DNA polymerase Phusion Flash II (ThermoFisher Scientific), 1× Access Array Harvest Solution (Fluidigm, PN 100-1031), 20× Access Array Loading reagent (Fluidigm), and the 266 primer pairs designed as described above. Instruments used for this amplification protocol included two IFC Controller AX (Fluidigm) and one FC1 cycler (Fluidigm).

Indexing (Also Known as Barcoding)

After cell-free DNA was amplified, the amplified DNA was indexed using index sequences, also called barcodes or tags. Indexing may be done, for example, to uniquely identify which of the three samples any detected amplified DNA originated from if cell-free DNA molecules from all of the samples are to be sequenced together. The amplified cell-free DNA was indexed according to the Fluidigm Access Array process and protocols (See page 70 of Access Array System for Illumina Sequencing System). Materials used for this indexing protocol included the high-fidelity polymerase Phusion Hot Start II (ThermoFisher Scientific), and an Access Array Barcode Library for Illumina Sequencers (Fluidigm—also called an index library). Instruments used included a PCR machine, a plate centrifuge, and a vortexer.

Sequencing

After the cell-free DNA was amplified and indexed, it was sequenced. The indexed cell-free DNA was sequenced according to Fluidigm/Illumina sequencing protocols for multiplex sequencing (See page 134 of Access Array System for Illumina Sequencing System). Materials used for this sequencing protocol included FL1 and FL2 sequencing primers (Fluidigm), HT1 buffer (Illumina), and a MiSeq Reagent Kit v3 (Illumina). Cell-free DNA was sequenced using a MiSeq sequencing instrument (Illumina).

Data Analysis

After the cell-free DNA was sequenced, it was analyzed to determine the presence and/or quantity of various SNP alleles (See FIG. 7 for general outline). Primary analysis involved the generation of FASTQ output files from the MiSeq instrument. Secondary analysis involved alignment of the output sequences sequenced by MiSeq to the human genome reference sequence. End trimming was performed using the "Cutadapt" and "TrimGalore" software packages. The alignment software "BWA" was used to conduct the alignment to the genomic regions encompassing the set of amplified amplicons. After alignment was complete, variant frequencies were assigned using the "SAMtools" software program and settings customized to minimize inclusion of sequencing errors.

Tertiary analysis of this type of data generally involves quality control aspects of the analysis. Data is analyzed to ensure that the minimum number of reads have been reached to achieve sufficient counting for each SNP position and ensure that there are not additional alleles present in the recipient. Data is also analyzed to ensure that the minimum and maximum number of SNP loci above background and below the heterozygous call level has been reached. These lower (background) and upper (transplant recipient heterozygous loci) limits may vary. In addition, there are metrics to ensure sufficient input DNA to achieve accurate measurement by determining the quality of the heterozygous SNP data. Further, genomic DNA may be determined and a cutoff assigned.

Methods used in the tertiary data determined the levels of donor-derived cell-free DNA in a given sample. The analysis included adjusting the minor allele frequency of the SNPs for sequencing or amplification errors by subtracting an empirically determined error rate for each transition or transversion, determining the set of SNPs that have a minor allele frequency lower than a cutoff between 0.1 to 0.25 as homozygous in the recipient, then using the level of the minor allele in these SNPs for calculation of donor contribution as a percent of the total cell-free DNA. SNPs with values less than 0.0008 minor allele frequency were removed. The median of the lower 55.4% of the remaining SNPs was doubled and averaged with the median of the highest 44.6% of the SNPs to estimate the donor contribution.

Determining Status of the Transplanted Organ

Figure 5:
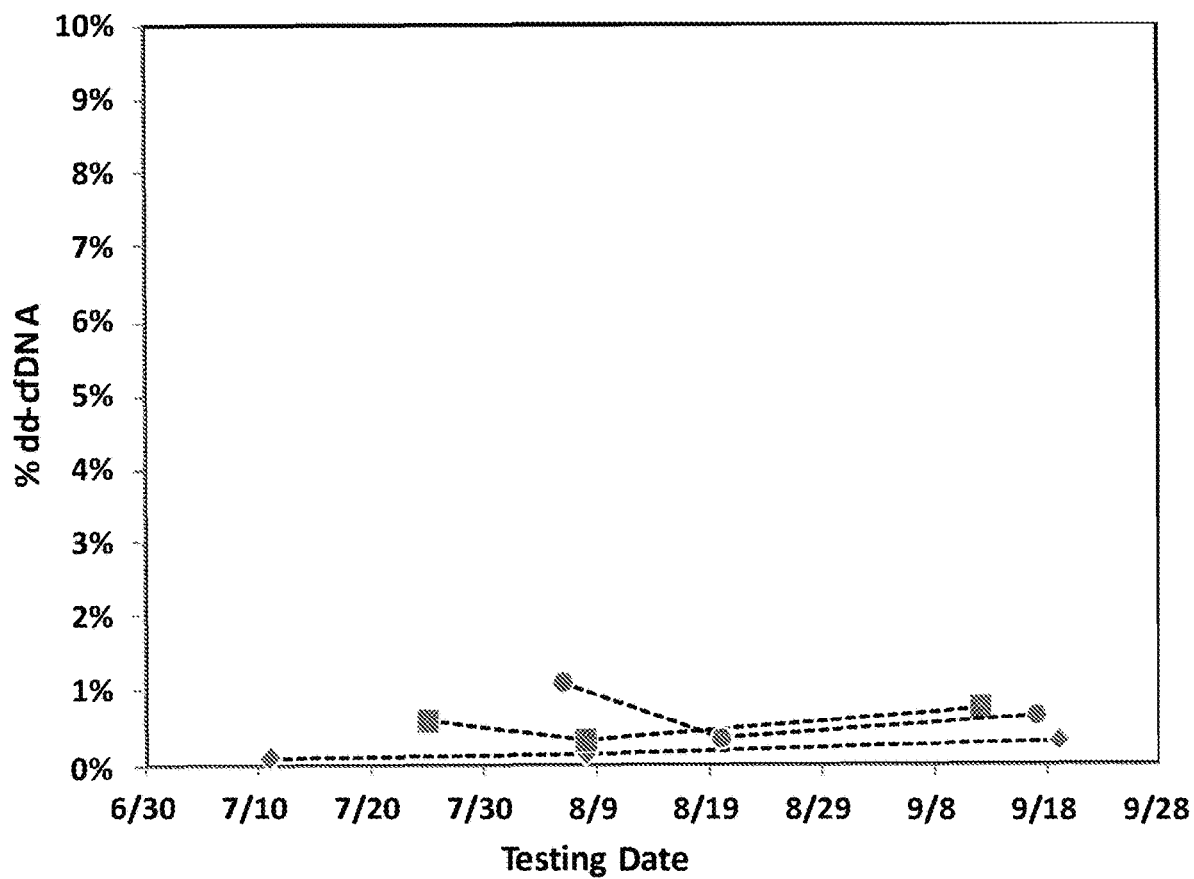
FIG. 5 illustrates dd-cfDNA values from Streck BCT plasma collection tubes following heart transplantation. Patient samples were blinded to rejection status or outcome. Three subjects, three visits each, each a different shape symbol. Donor-derived cell-free DNA is expressed as a percent of the total cell-free DNA, measured as described herein.

The data analysis methods described above were used to determine the level of donor-derived cell-free DNA in each of the cell-free DNA samples obtained from the transplant recipients. The data analysis involved comparison of the levels of donor-derived cell-free DNA in each of the samples to the other samples from that patient to determine if the levels of donor-derived cell-free DNA were increasing, decreasing, or were being maintained at relatively constant levels in cell-free DNA isolated from the transplant recipient over time. An increase in the levels or variance of the donor-derived cell-free DNA over time is indicative of transplant rejection as shown in FIG. 1. FIG. 5 shows the stable nature of percent donor-derived cell-free DNA. This suggests that the physician will not need to adjust immunosuppressive therapy in these stable patients.

Example 7—Analysis of Cell-Free DNA to Determine Status of Transplanted Organ in a Heart Transplant Recipient in Combination with a Gene Expression Test This Example demonstrates the analysis of samples containing cell-free DNA from a set of 55 transplant recipients to determine the level of donor-derived cell-free DNA in the samples. In addition, samples containing RNA from peripheral blood mononuclear cells were used to determine the levels of gene expression as measured using AlloMap Molecular Expression Testing. Levels of donor-derived cell-free DNA and gene expression were used to diagnose the status of the transplanted organ in the transplant recipient and predict future status of the transplanted organ, as well as inform the need to adjust or maintain immunosuppressive therapies being administered to the transplant recipient.

Subject Selection

Human patients were selected who were the subject of a heart transplant prior to this assay as described in this Example. The patients were undergoing treatment with immunosuppressive therapy to prevent rejection of the allograft. Separate plasma samples and peripheral blood mononuclear cell lysates were collected from these subjects at visits dictated by the standard of care at their respective centers. The methods described in this Example are applicable to one or more of the samples isolated from the transplant recipient.

Rna Collection, Processing, and Testing

Peripheral blood mononuclear cells (PBMC) were collected, RNA stabilized, RNA isolated, cDNA created, and cDNA measured by real-time quantitative PCR as described for AlloMap Molecular Expression Testing, an FDA-cleared gene expression profile used to monitor clinically stable heart transplant recipients.

Plasma Collection

Blood was extracted from the subjects so that cell-free DNA could be extracted from plasma isolated from the blood sample. The blood sample was collected in PPT tubes according to the venipuncture method as previously described (Clinical and Laboratory Standards Institute, 2012). The PPT tube (Plasma Preparation Tube, Becton Dickinson) was filled completely with the blood sample. The tube was removed from the adapter and was immediately mixed by gentle inversion. After collection, the tubes were centrifuged according to the manufacturer's protocol and stored at −80° C. Upon processing of the sample, the tube was thawed and the plasma layer was carefully removed and transferred to a clean tube. This plasma sample was then centrifuged at 1600×g for 10 minutes at room temperature, the supernatant removed and placed into a new tube and centrifuged at 16,000×g for 10 minutes at room temperature. The resulting plasma layer was carefully removed and placed into a new tube, and the plasma sample then proceeded to have cell-free DNA (cf DNA) extracted.

Cell-Free DNA (cfDNA) Extraction

Approximately 1 mL of plasma from the plasma sample was used to proceed with cell-free DNA extraction. For PPT plasma preparation tubes (Becton Dickinson), page 22 of the Qiagen protocol (QIAamp Circulating Nucleic Acid Handbook, 2011) was used with the following modifications: at step 15 on page 25, elute with 21 µL Buffer AVE.

SNP Selection

Various SNPs were selected for analysis to estimate the percentage of donor-derived cfDNA present in the subject's plasma sample. The SNPs selected for analysis were rs10488710, rs279844, rs1048290, rs1049379, rs1051614, rs1052637, rs1055851, rs1056033, rs1056149, rs1064074, rs1078004, rs10831567, rs6811238, rs11106, rs11210490, rs1126899, rs1127472, rs1127893, rs1130857, rs1049544, rs11547806, rs12237048, rs430046, rs12508837, rs12529, rs12717, rs13184586, rs13295990, rs13428, rs13436, rs1374570, rs14080, rs1411271, rs576261, rs14155, rs1151687, rs1565933, rs1600, rs1678690, rs1881421, rs1897820, rs1898882, rs2056844, rs20575, rs10092491, rs2070426, rs2071888, rs2075322, rs2180314, rs2185798, rs2227910, rs2228560, rs2229571, rs2229627, rs2245285, rs2342747, rs2248490, rs2253592, rs2254357, rs2275047, rs2279665, rs2279776, rs2281098, rs2287813, rs4364205, rs2289751, rs2289818, rs2292830, rs2294092, rs2295005, rs2296545, rs2297236, rs2302443, rs2306049, rs1022478, rs445251, rs230898, rs231235, rs2342767, rs236152, rs2362450, rs2384571, rs2455230, rs246703, rs2480345, rs248385, rs2498982, rs2505232, rs2509943, rs2519123, rs2523072, rs2571028, rs2657167, rs28686812, rs2946994, rs1294331, rs10419826, rs3088241, rs3110623, rs3173615, rs3190321, rs3205187, rs344141, rs35596415, rs362124, rs36657, rs1872575, rs159606, rs3731877, rs3734311, rs3735615, rs3740199, rs3748930, rs3751066, rs3790993, rs3802265, rs3803763, rs1004357, rs3803798, rs3809972, rs3810483, rs3812571, rs3813609, rs3814182, rs3816800, rs3826709, rs3829655, rs3951216, rs1019029, rs408600, rs41317515, rs436278, rs448012, rs475002, rs4845480, rs4849167, rs4865615, rs1027895, rs4890012, rs492594, rs4940019, rs4971514, rs523104, rs528557, rs545500, rs561930, rs57010808, rs57285449, rs10500617, rs6061243, rs609521, rs62490396, rs625223, rs638405, rs6459166, rs648802, rs6510057, rs6764714, rs10768550, rs6790129, rs6794, rs6807362, rs6838248, rs713598, rs7161563, rs726009, rs7289, rs7301328, rs7332388, rs10773760, rs743616, rs743852, rs745142, rs7451713, rs7526132, rs7543016, rs7601771, rs7785899, rs7825, rs8009219, rs10776839, rs8025851, rs8058696, rs8076632, rs8097, rs8103906, rs874881, rs9262, rs9289122, rs936019, rs9393728, rs1109037, rs977070, rs9865242, rs12480506, rs560681, rs12997453, rs13134862, rs13218440, rs1358856, rs1410059, rs1478829, rs1498553, rs1523537, rs4606077, rs1554472, rs1736442, rs1821380, rs2046361, rs214955, rs2175957, rs2255301, rs2269355, rs2270529, rs2272998, rs2291395, rs2292972, rs2399332, rs2503107, rs2567608, rs2811231, rs2833736, rs315791, rs321198, rs6955448, rs338882, rs3780962, rs4288409, rs4530059, rs464663, rs4789798, rs4796362, rs4847034, rs521861, rs1058083, rs5746846, rs590162, rs6444724, rs6591147, rs689512, rs7205345, rs722290, rs740598, rs7520386, rs221956, rs7704770, rs8070085, rs8078417, rs891700, rs901398, rs9546538, rs9606186, rs985492, rs9866013, rs987640, rs13182883, rs9905977, rs993934, rs9951171, rs10274334, rs10421285, rs1043413, rs1044010, rs1045248, rs1045644, and rs1047979. To amplify the SNPs, 266 primer pairs were designed (Fluidigm).

DNA Pre-Amplification

To amplify targeted regions which include SNPs of interest in the cell-free DNA, various materials were assembled and used in the amplification process. The Phusion Hot Start II DNA Polymerase (ThermoFisher Scientific) was used. 266 primer pairs were designed and produced (IDT or Fluidigm per Fluidigm design). ExoI and ExoI buffer (New England BioLabs) were used. Methods followed included the Fluidigm pre-amplification protocol (See Page 152 of Access Array System for Illumina Sequencing System). Instruments used included a PCR machine, a plate centrifuge, and a vortexer.

DNA Amplification

The cell-free DNA from the pre-amplification was amplified according to the Fluidigm Access Array process and protocols (See page 63 of Access Array System for Illumina Sequencing System). Materials used for this amplification protocol included a Fluidigm Access Array, or chip, the high-fidelity DNA polymerase Phusion Flash II (ThermoFisher Scientific), 1× Access Array Harvest Solution (Fluidigm, PN 100-1031), 20× Access Array Loading reagent (Fluidigm), and the 266 primer pairs designed as described above. Instruments used for this amplification protocol included two IFC Controller AX (Fluidigm) and one FC1 cycler (Fluidigm).

Indexing (Also Known as Barcoding)

After cell-free DNA was amplified, the amplified DNA was indexed using index sequences, also called barcodes or tags. Indexing may be done, for example, to uniquely identify which of the three samples any detected amplified DNA originated from if cell-free DNA molecules from all of the samples are to be sequenced together. The amplified cell-free DNA was indexed according to the Fluidigm Access Array process and protocols (See page 70 of Access Array System for Illumina Sequencing System). Materials used for this indexing protocol included the high-fidelity polymerase Phusion Hot Start II (ThermoFisher Scientific), and an Access Array Barcode Library for Illumina Sequencers (Fluidigm—also called an index library). Instruments used included a PCR machine, a plate centrifuge, and a vortexer.

Sequencing

After the cell-free DNA was amplified and indexed, it was sequenced. The indexed cell-free DNA was sequenced according to Fluidigm/Illumina sequencing protocols for multiplex sequencing (See page 134 of Access Array System for Illumina Sequencing System). Materials used for this sequencing protocol included FL1 and FL2 sequencing primers (Fluidigm), HT1 buffer (Illumina), and a MiSeq Reagent Kit v3 (Illumina). Cell-free DNA was sequenced using a MiSeq sequencing instrument (Illumina).

Cfdna Data Analysis

After the cell-free DNA was sequenced, it was analyzed to determine the presence and/or quantity of various SNP alleles (See FIG. 7 for general outline). Primary analysis involved the generation of FASTQ output files from the MiSeq instrument. Secondary analysis involved alignment of the output sequences sequenced by MiSeq to the human genome reference sequence. End trimming was performed using the "Cutadapt" and "TrimGalore" software packages. The alignment software "BWA" was used to conduct the alignment to the genomic regions encompassing the set of amplified amplicons. After alignment was complete, variant frequencies were assigned using the "SAMtools" software program and settings customized to minimize inclusion of sequencing errors.

Tertiary analysis of this type of data generally involves quality control aspects of the analysis. Data is analyzed to ensure that the minimum number of reads have been reached to achieve sufficient counting for each SNP position and ensure that there are not additional alleles present in the recipient. Data is also analyzed to ensure that the minimum and maximum number of SNP loci above background and below the heterozygous call level has been reached. These lower (background) and upper (transplant recipient heterozygous loci) limits may vary. In addition, there are metrics to ensure sufficient input DNA to achieve accurate measurement by determining the quality of the heterozygous SNP data. Further, genomic DNA may be determined and a cutoff assigned.

Methods used in the tertiary data determined the levels of donor-derived cell-free DNA in a given sample. The analysis included adjusting the minor allele frequency of the SNPs for sequencing or amplification errors by subtracting an empirically determined error rate for each transition or transversion, determining the set of SNPs that have a minor allele frequency lower than a cutoff between 0.1 to 0.25 as homozygous in the recipient, then using the level of the minor allele in these SNPs for calculation of donor contribution as a percent of the total cell-free DNA. SNPs with values less than 0.0008 minor allele frequency were removed. The median of the lower 55.4% of the remaining SNPs was doubled and averaged with the median of the highest 44.6% of the SNPs to estimate the donor contribution.

Determining Status of the Transplanted Organ

Figure 6A:
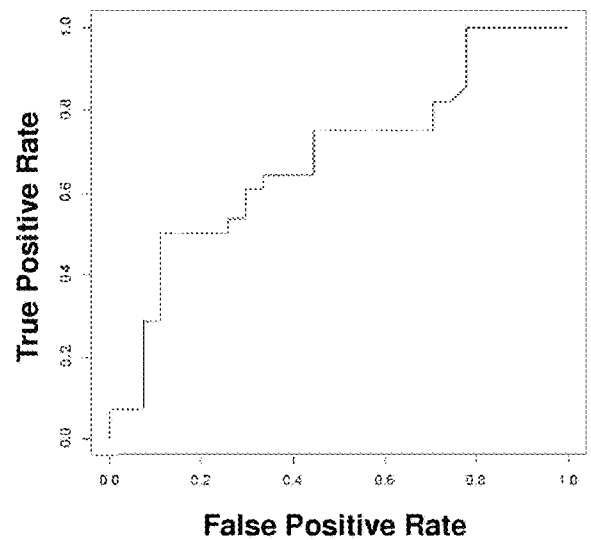
FIG. 6A-FIG. 6C illustrates that dd-cfDNA is a signal unique from gene expression profiling of blood markers, and the combination of both can better identify rejection.
Figure 6B:
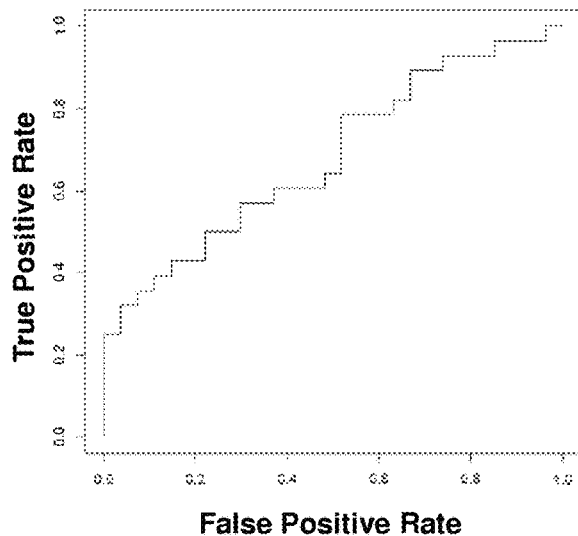
Figure 6C:
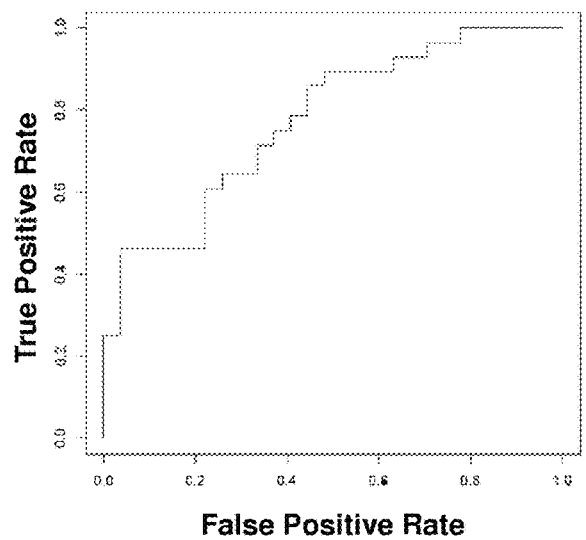

The data analysis methods described above were used to determine the level of donor-derived cell-free DNA in each of the cell-free DNA samples obtained from the transplant recipients. The data analysis involved comparison of the levels of donor-derived cell-free DNA in each of the samples to the other samples from that patients to determine if the levels of donor-derived cell-free DNA was increasing, decreasing, or was being maintained at relatively constant levels in cell-free DNA isolated from the transplant recipients over time. An increase in the levels or variance of the donor-derived cell-free DNA over time is indicative of transplant rejection as shown in FIG. 1 and FIG. 6A. These two figures show the relationship between well-characterized rejection and high percent donor-derived cell-free DNA. FIG. 6B shows the relationship between well-characterized rejection and the results of AlloMap Molecular Expression Testing for the gene expression signature. FIG. 6C shows the ability of a combined result from donor-derived cell-free DNA and gene expression to better discriminate between rejection and non-rejection. The two values (percent dd-cfDNA and AlloMap) were scaled to the same range and then additively combined to create a single score. This suggests that the physician will have better information about the status of the transplanted organ if both cfDNA and gene expression are used and combined in this way or similar methods.

REFERENCES

Clinical and Laboratory Standards Institute. H3-A6, (2012) Procedures for the Collection of Diagnostic Blood Specimens by Venipuncture; Approved Standard-Sixth Edition, Vol. 27, No. 26.

QIAamp Circulating Nucleic Acid Handbook, (2011), Second Edition.

Pakstis AJ, Speed WC, Fang R, Hyland FC, Furtado MR, Kidd JR, Kidd KK. (2010) SNPs for a universal individual identification panel. Hum Genet; 127 (3): 315-24.

Access Array System for Illumina Sequencing System, P/N 100-3770, Rev. G1.

Andreas Wilm, Pauline Poh Kim Aw, Denis Bertrand, Grace Hui Ting Yeo, Swee Hoe Ong, Chang Hua Wong, Chiea Chuen Khor, Rosemary Petric, Martin Lloyd Hibberd and Niranjan Nagarajan. (2012) LoFreq: A sequence-quality aware, ultra-sensitive variant caller for uncovering cell-population heterogeneity from high-throughput sequencing datasets. Nucleic Acids Res. 40 (22): 11189-201.

What is claimed is:

1. A method for sequencing, comprising:
   (a) providing a sample of a subject, wherein said sample comprises a plurality of cell-free nucleic acid molecules, and wherein said subject is a recipient of an allograft;
   (b) isolating said plurality of cell-free nucleic acid molecules from said sample;
   (c) amplifying said plurality of cell-free nucleic acid molecules to generate a plurality of amplified nucleic acid molecules;
   (d) subjecting said plurality of amplified nucleic acid molecules, or derivatives thereof, to one or more amplification reactions using a plurality of primers to generate a plurality of deoxyribonucleic acid ("DNA") molecules, wherein said plurality of primers target at least 100 independent polymorphisms; and
   (e) sequencing said plurality of DNA molecules, or derivatives thereof,
   wherein genotyping of said subject is not performed.

2. The method of claim 1, wherein said one or more amplification reactions comprises polymerase chain reaction (PCR).

3. The method of claim 1, further comprising purifying said plurality of DNA molecules, or derivatives thereof.

4. The method of claim 1, wherein said sequencing in (e) comprises detecting an optical signal from a probe coupled to a DNA molecule or a derivative thereof of said plurality of DNA molecules or derivatives thereof.

5. The method of claim 1, wherein said sample is derived from blood.

6. The method of claim 1, wherein said sample comprises peripheral blood mononuclear cells.

7. The method of claim 1, wherein said sample is plasma.

8. The method of claim 1, wherein said plurality of amplified nucleic acid molecules in (d) are amplified using a panel that differentiates between cell-free nucleic acid molecules of said plurality of cell-free nucleic acid molecules.

9. The method of claim 1, further comprising barcoding said plurality of cell-free nucleic acid molecules prior to (c).

10. The method of claim 1, wherein said allograft is a kidney, a liver, a lung, a heart, a pancreas, a cornea transplant, a skin transplant, an organ system transplant, a xenotransplant, a bone marrow transplant, a stem cell transplant, or a combination thereof.

11. The method of claim 1, wherein two or more polymorphisms of said at least 100 independent polymorphisms comprise single nucleotide polymorphisms (SNPs).

12. The method of claim 1, wherein two or more polymorphisms of said at least 100 independent polymorphisms are homozygous in said subject.

13. The method of claim 1, further comprising obtaining a second sample from said subject.

14. The method of claim 13, wherein said second sample comprises peripheral blood mononuclear cells (PBMCs).

15. The method of claim 14, wherein said second sample comprises a plurality of nucleic acid molecules comprising ribonucleic acid (RNA) molecules isolated from said PBMCs.

16. The method of claim 1, wherein said sequencing is next generation sequencing.

17. The method of claim 1, wherein said allograft is obtained from a donor, and wherein genotyping of said donor is not performed.

18. The method of claim 1, wherein said plurality of primers target at least 105 independent polymorphisms.

19. The method of claim 1, wherein said plurality of primers target at least 110 independent polymorphisms.

20. The method of claim 1, wherein said plurality of primers target at least 115 independent polymorphisms.

21. The method of claim 1, wherein said plurality of primers target at least 120 independent polymorphisms.

22. The method of claim 1, wherein said plurality of primers target at least 150 independent polymorphisms.

\* \* \* \* \*